United States Patent
Franczyk, II et al.

(10) Patent No.: US 8,168,784 B2
(45) Date of Patent: May 1, 2012

(54) PROCESSES TO MAKE APOPTOSIS PROMOTERS

(75) Inventors: Thaddeus Stephan Franczyk, II, Lake Villa, IL (US); David R. Hill, Gurnee, IL (US); Anthony Ralph Haight, Wadsworth, IL (US); Maureen Ann McLaughlin, Kenosha, WI (US); Shashank Shekhar, Highland Park, IL (US); Su Yu, Lake Bluff, IL (US); Jianzhang Mei, Lake Forest, IL (US); Lei Wang, Acton, MA (US)

(73) Assignee: Abbott Laboratories, Abbott Park, IL (US)

( * ) Notice: Subject to any disclaimer, the term of this patent is extended or adjusted under 35 U.S.C. 154(b) by 372 days.

(21) Appl. No.: 12/486,361

(22) Filed: Jun. 17, 2009

(65) Prior Publication Data
US 2009/0318689 A1     Dec. 24, 2009

Related U.S. Application Data

(60) Provisional application No. 61/074,390, filed on Jun. 20, 2008.

(51) Int. Cl.
| C07D 413/12 | (2006.01) |
| C07C 47/42 | (2006.01) |
| C07C 49/403 | (2006.01) |

(52) U.S. Cl. .............. 544/121; 568/376; 568/425
(58) Field of Classification Search ................ None
See application file for complete search history.

(56) References Cited

U.S. PATENT DOCUMENTS
| 7,390,799 B2 | 6/2008 | Bruncko et al. |
| 2005/0159427 A1 | 7/2005 | Bruncko et al. |
| 2007/0027135 A1 | 2/2007 | Bruncko et al. |

FOREIGN PATENT DOCUMENTS
WO    2008061208 A2    5/2008

OTHER PUBLICATIONS

Bielawski, et al. "Regiospecific One-Pot Synthesis of Diaryliodonium Tetrafluoroborates from Arylboronic Acids and Aryl Iodides", J Org Chem, vol. 73 pp. 4602-4607, 2008.
Carroll, et al. "New synthesis of diaryliodonium sulfonates from arylboronic acids" Tetrahedron Letters, vol. 41, pp. 5393-5396, 2000.
Kalyani, et al. "Oxidative C-H Activiation/C-C Bond Forming Reactions: Synthetc Scope and Mechanistic Insights", J Am Chem Soc, vol. 127, pp. 7330-7331, 2005.
Wang, et al. "An efficient Synthesis of ABT-263, A Novel Inhibitor of Antiapoptotic Bcl-2 Proteins", Synthesis, vol. 15, pp. 2398-2404, 2008.
The PCT International Search Report, PCT/US2009/047723, Date of mailing Oct. 21, 2009.

*Primary Examiner* — Rebecca Anderson
*Assistant Examiner* — Alicia L Otton
(74) *Attorney, Agent, or Firm* — Armstrong Teasdale LLP

(57) ABSTRACT

Processes to make compounds, including N-acylsulfonamide apoptosis promoters are disclosed.

10 Claims, No Drawings

PROCESSES TO MAKE APOPTOSIS PROMOTERS

RELATED APPLICATION INFORMATION

This application claims priority to U.S. Provisional Patent Application Ser. No. 61/074390, filed Jun. 20, 2008, which is incorporated by reference in its entirety.

FIELD OF THE INVENTION

The present invention relates to, among other things, novel compounds and synthetic processes, including those useful for making N-acylsulfonamide apoptosis promoters.

BACKGROUND OF THE INVENTION

Novel N-acylsulfonamide apoptosis promoters are described in, for example, U.S. Patent Publication US2005/0159427A1, U.S. Pat. No. 7,390,799 B2 (referred to hereinafter as the "'799 Patent") and elsewhere. Synthetic routes for the preparation of N-acylsulfonamide apoptosis promoters are described in the '799 Patent and K. Ding, et al. (*Synthesis*, 2008, 15, 2398-2404).

SUMMARY OF THE INVENTION

The present invention provides, among other things, safe, efficient and cost-effective processes for making N-acylsulfonamide apoptosis promoters.

One aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and a first fluoride source to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent (CH$_3$SiCF$_3$), and a second fluoride source to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first NH$_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-((((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(r) reacting a first metal trifluoromethanesulfinate, a first aryl fluoride source, and a first catalyst to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first NH$_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-((((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4- dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethyl-cyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl) methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl) oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethyl-cyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl) methyl)piperazin-1-yl)benzoic acid;

(m) reacting 2-fluorobenzenesulfonyl chloride, and tetra-n-butylammonium fluoride to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid;

(r) reacting sodium trifluoromethanesulfinate, bis-(2-fluorophenyl)iodonium tetrafluoroborate and copper(I) oxide to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide and a first coupling reagent with or without a fourth base and with or without an auxiliary coupling reagent, and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Another aspect of this invention pertains to a compound, or a pharmaceutically acceptable salt thereof, chosen from (2E)-4,4-dimethyl-2-(((triisopropylsilyl)oxy)methylene)cyclohexanone, (2E)-4,4-dimethyl-2-(((trimethylsilyl)oxy)methylene)cyclohexanone, and (2E)-2-(((tert-butyl(dimethyl)silyl)oxy)methylene)-4,4-dimethylcyclohexanone.

Another aspect of this invention pertains to 2-(4-chlorophenyl)-5,5-dimethylcyclohex-1-ene-1-carbaldehyde or a pharmaceutically acceptable salt thereof.

DETAILED DESCRIPTION OF THE INVENTION

Variable moieties are represented by identifiers (capital letters with numerical and/or alphabetical superscripts) and may be specifically embodied.

The term "alkyl," as used herein, means $C_1$-alkyl, $C_2$-alkyl, $C_3$-alkyl, $C_4$-alkyl, $C_5$-alkyl, and $C_6$-alkyl.

The term "$C_1$-alkyl," as used herein, means methyl.

The term "$C_2$-alkyl," as used herein, means ethyl.

The term "$C_3$-alkyl," as used herein, means prop-1-yl and prop-2-yl (isopropyl).

The term "$C_4$-alkyl," as used herein, means but-1-yl, but-2-yl, 2-methylprop-1-yl, and 2-methylprop-2-yl (tert-butyl).

The term "$C_5$-alkyl," as used herein, means 2,2-dimethylprop-1-yl (neo-pentyl), 2-methylbut-1-yl, 2-methylbut-2-yl, 3-methylbut-1-yl, 3-methylbut-2-yl, pent-1-yl, pent-2-yl, and pent-3-yl.

The term "$C_6$-alkyl," as used herein, means 2,2-dimethylbut-1-yl, 2,3-dimethylbut-1-yl, 2,3-dimethylbut-2-yl, 3,3-dimethylbut-1-yl, 3,3-dimethylbut-2-yl, 2-ethylbut-1-yl, hex-1-yl, hex-2-yl, hex-3-yl, 2-methylpent-1-yl, 2-methylpent-2-yl, 2-methylpent-3-yl, 3-methylpent-1-yl, 3-methylpent-2-yl, 3-methylpent-3-yl, 4-methylpent-1-yl, and 4-methylpent-2-yl.

The term "alcohol," as used herein, means methanol, ethanol, isopropanol, tert-butanol, and the like or a mixture thereof.

The term, "bis-(2-fluorophenyl)iodonium alkyl-sulfonate," as used herein means bis-(2-fluorophenyl)iodonium methylsulfonate, bis-(2-fluorophenyl)iodonium hexanesulfonate, bis-(2-fluorophenyl)iodonium dodecanesulfonate, bis-(2-fluorophenyl)iodonium trifluromethylsulfonate, bis-(2-fluorophenyl)iodonium allylsulfonate, bis-(2-fluorophenyl)iodonium poly(vinyl)sulfonate and the like.

The term, "bis-(2-fluorophenyl)iodonium aryl-sulfonate," as used herein means bis-(2-fluorophenyl)iodonium benzenesulfonate, bis-(2-fluorophenyl)iodonium p-toluenesulfonate, bis-(2-fluorophenyl)iodonium mesitylsulfonate, bis-(2-fluorophenyl)iodonium naphthylsulfonate and the like.

The term, "bis-(2-fluorophenyl)iodonium cycloalkyl-sulfonate," as used herein means bis-(2-fluorophenyl)iodonium cyclopropylsulfonate, bis-(2-fluorophenyl)iodonium cyclohexylsulfonate and the like.

The term, "bis-(2-fluorophenyl)iodonium heterocycle-sulfonate," as used herein means bis-(2-fluorophenyl)iodonium thiophenylsulfonate, bis-(2-fluorophenyl)iodonium-2-pyridylsulfonate, bis-(2-fluorophenyl)iodonium-3-pyridylsulfonate, bis-(2-fluorophenyl)iodonium furfuryl-5-sulfonate, bis-(2-fluorophenyl)iodonium indonylsulfonate, and the like.

Compounds of this invention can have one or more than one asymmetrically substituted carbon atoms in the R or S configuration. Compounds having asymmetrically substituted carbon atoms enriched with one configuration over the other are assigned the configuration which is present in the higher amount, preferably 85% to 95% enrichment, more preferably 95% to 99% enrichment, and still more preferably greater than 99% enrichment. Accordingly, compounds of this invention can exist as enantiomers, mixtures of enantiomers, diastereomers having relative stereochemistry, diastereomers having absolute stereochemistry, diastereomers having at least one asymmetrically substituted carbon atom which is enriched in one configuration and at least one asymmetrically substituted carbon atom which is not enriched, and mixtures of the preceding.

Compounds of this invention can also have one or more than one carbon-carbon double bond or carbon-nitrogen double bond. Accordingly, compounds of this invention can exist as geometric isomers of either Z or E configuration or as mixtures of geometric isomers.

The terms "R", "S", "Z", and "E" are as defined by the IUPAC 1974 Recommendations for Section E, Fundamental Stereochemistry, Pure Appl. Chem. (1976) 45, 13-10.

Compounds of this invention may exist as acid addition salts or base addition salts and may be prepared during their isolation or following their purification. Acid addition salts of compounds are prepared by reaction with acid. For example, the acetate, adipate, alginate, bicarbonate, citrate, aspartate, benzoate, benzenesulfonate, bisulfate, butyrate, camphorate, camphorsufonate, citrate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetate, trifluoroacetate, para-toluenesulfonate, and undecanoate salts of compounds of this invention are meant to be embraced thereby. Base addition salts of compounds of this invention may be prepared by reaction with a base such as the hydroxide, carbonate, bicarbonate, phosphate, hydrogen phosphate, or dihydrogen phosphate of cations such as calcium, iron, lithium, potassium, sodium or magnesium.

The term "isolating" as used herein, means separating a compound from a solvent, anti-solvent, or a mixture of solvent and anti-solvent to provide a solid, semisolid or syrup. This is typically accomplished by means such as centrifugation, filtration with or without vacuum, filtration under positive pressure, distillation, evaporation or a combination thereof. Isolating may or may not include purifying during which the chemical, chiral or chemical and chiral purity of the isolate is increased. Purifying is typically conducted by means such as crystallization, distillation, extraction, filtration through acidic, basic or neutral alumina, filtration through acidic, basic or neutral charcoal, column chromatography on a column packed with a chiral stationary phase, filtration through a porous paper, plastic or glass barrier, column chromatography on silica gel, ion exchange chromatography, recrystallization, normal-phase high performance liquid chromatography, reverse-phase high performance liquid chromatography, trituration and the like.

The phrase "isolating or not isolating" as used herein, means that during the practice of this invention, it is optional to isolate a particular compound after each step prior to the next step. Such a decision can easily be made by one of ordinary skill in the art, based on stability, purity, solvent conditions of the next step, etc.

The exemplified compounds and intermediates were named using ACD/ChemSketch Version 5.06 (5 Jun. 2001, Advanced Chemistry Development Inc., Toronto, Ontario), or ChemDraw® Ver. 9.0.5 (CambridgeSoft, Cambridge, Mass.). N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide was named as in the '799 Patent.

Synthetic routes to prepare 4-fluoro-3-((trifluoromethyl)sulfonyl)benzenesulfonamide, and 4-(4-((2-(4-chlorophenyl)-5,5-dimethylcyclohex-1-en-1-yl)methyl)piperazin-1-yl)benzoic acid, intermediates in the synthesis of apoptosis promoters are described in the '799 Patent, and K. Ding, et al. (*Synthesis*, 2008, 15, 2398-2404, referred to hereinafter as the Ding reference). The '799 Patent describes a synthesis using trifluoromethyl iodide, a gas with toxicity concerns. Also, the subsequent oxidation step uses $RuCl_3$ and $NaIO_4$, creating a highly exothermic reaction. The Ding reference describes numerous chemical steps to make 4-(4-((2-(4-chlorophenyl)-5,5-dimethylcyclohex-1-en-1-yl)methyl)piperazin-1-yl)benzoic acid and lower overall yield. In addition, the very high reaction temperatures are not readily achievable or ideal on a large scale. Finally, the synthesis described in the Ding reference utilizes a relatively expensive starting material.

The present inventors previous explorations of the synthesis described in the Ding, et al. reference identified a number of problems. First of all, the chemistry used is burdened with a potential genotoxic liability due to brominated products created when hydrobromic and trifluoroacetic acids are used together. Also, when these or other acids such as methanesulfonic acid were used, multiple impurities were generated which were inefficiently and ineffectively removed by typical purification methods such as crystallization. Yield, purity and processing time were compromised as a result. Finally, poor physical properties of isolated intermediates made filtrations slow and inefficient.

The present invention avoids these disadvantages.

Embodiments

One embodiment of this invention, therefore, pertains to a process for making a protected (2E)-2-(hydroxymethylene)-4,4-dimethylcyclohexanone, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone; and (b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone.

Another embodiment pertains to (2E)-4,4-dimethyl-2-(((triisopropylsilyl)oxy)methylene)cyclohexanone, (2E)-4,4-dimethyl-2-(((trimethylsilyl)oxy)methylene)cyclohexanone, and (2E)-2-(((tert-butyl(dimethyl)silyl)oxy)methylene)-4,4-dimethylcyclohexanone, or a pharmaceutically acceptable salt thereof, prepared as described in the preceding embodiment.

Another embodiment pertains to the compound (2E)-4,4-dimethyl-2-(((triisopropylsilyl)oxy)methylene)cyclohexanone or a pharmaceutically acceptable salt thereof.

Another embodiment pertains to (2E)-4,4-dimethyl-2-(((triisopropylsilyl)oxy)methylene)cyclohexanone, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a pharmaceutically acceptable salt thereof.

Another embodiment pertains to (2E)-4,4-dimethyl-2-(((triisopropylsilyl)oxy)methylene)cyclohexanone, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203, which are hereby incorporated by reference.

Another embodiment pertains to the compound (2E)-4,4-dimethyl-2-(((trimethylsilyl)oxy)methylene)cyclohexanone, or a pharmaceutically acceptable salt thereof.

Another embodiment pertains to (2E)-4,4-dimethyl-2-(((trimethylsilyl)oxy)methylene)cyclohexanone, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a pharmaceutically acceptable salt thereof.

Another embodiment pertains to (2E)-4,4-dimethyl-2-(((trimethylsilyl)oxy)methylene)cyclohexanone, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Another embodiment pertains to the compound (2E)-2-(((tert-butyl(dimethyl)silyl)oxy)methylene)-4,4-dimethylcyclohexanone, or a pharmaceutically acceptable salt thereof.

Another embodiment pertains to (2E)-2-(((tert-butyl(dimethyl)silyl)oxy)methylene)-4,4-dimethylcyclohexanone, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a pharmaceutically acceptable salt thereof.

Another embodiment pertains to (2E)-2-(((tert-butyl(dimethyl)silyl)oxy)methylene)-4,4-dimethylcyclohexanone, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Compounds described in U.S. Patent Publication US2005/0159427A1, the '799 Patent, and U.S. Provisional Applications 61/145611, 61/120275, 61/181180, and 61/181203, include 4-(4-((2-(4-chlorophenyl)-5,5-dimethylcyclohex-1-en-1-yl)methyl)piperazin-1-yl)-N-((4-(((1R)-3-(dimethylamino)-1-((phenylthio)methyl)propyl)amino)-3-nitrophenyl)sulfonyl)benzamide, 4-(4-((2-(4-chlorophenyl)-5,5-dimethylcyclohex-1-en-1-yl)methyl)piperazin-1-yl)-N-((4-(((1R)-3-(isopropyl(methyl)amino)-1-((phenylthio)methyl)propyl)amino)-3-((trifluoromethyl)sulfonyl)phenyl)sulfonyl)benzamide, 4-(4-((2-(4-chlorophenyl)-5,5-dimethylcyclohex-1-en-1-yl)methyl)piperazin-1-yl)-N-((5-(((1R)-3-(isopropyl(methyl)amino)-1-((phenylthio)methyl)propyl)amino)-4-nitrothien-2-yl)sulfonyl)benzamide, 4-(4-((2-(4-chlorophenyl)-5,5-dimethylcyclohex-1-en-1-yl)methyl)piperazin-1-yl)-N-((4-((3-morpholin-4-ylpropyl)amino)-3-nitrophenyl)sulfonyl)-2-phenoxybenzamide, 4-(4-((2-(4-chlorophenyl)-5,5-dimethylcyclohex-1-en-1-yl)methyl)piperazin-1-yl)-N-((3-nitro-4-((tetrahydro-2H-pyran-4-ylmethyl)amino)phenyl)sulfonyl)-2-(1H-pyrrolo(2,3-b)pyridin-5-yloxy)benzamide, and the like.

One embodiment of this invention, therefore, pertains to a process for making 2-(4-chlorophenyl)-5,5-dimethylcyclohex-1-ene-1-carbaldehyde, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Another embodiment pertains to 2-(4-chlorophenyl)-5,5-dimethylcyclohex-1-ene-1-carbaldehyde or a pharmaceutically acceptable salt thereof.

Another embodiment pertains to 2-(4-chlorophenyl)-5,5-dimethylcyclohex-1-ene-1-carbaldehyde, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a pharmaceutically acceptable salt thereof.

Another embodiment pertains to 2-(4-chlorophenyl)-5,5-dimethylcyclohex-1-ene-1-carbaldehyde, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Examples of alkyl formates useful for the practice of this invention are methyl formate, ethyl formate, n-propyl formate, tert-butyl formate and the like.

Examples of first bases useful for the practice of this invention are sodium hydride, sodium tert-butoxide, potassium tert-butoxide and the like.

Examples of second bases useful for the practice of this invention are triethylamine, 2,6-lutidine, pyridine, imidazole, diisopropylethylamine, N-methylmorpholine, dimethylaniline and the like.

Examples of first silyl ether protecting group reagents useful for the practice of this invention include trimethylchlorosilane, tert-butylchlorodimethylsilane, triisopropylchlorosilane, tert-butylchlorodiphenylsilane, and the like.

Examples of first protected (2E)-2-(hydroxymethylene)-4,4-dimethylcyclohexanones useful for the practice of this invention include (2E)-4,4-dimethyl-2-(((triisopropylsilyl)oxy)methylene)cyclohexanone, (2E)-4,4-dimethyl-2-(((trimethylsilyl)oxy)methylene)cyclohexanone, (2E)-2-(((tert-butyl(dimethyl)silyl)oxy)methylene)-4,4-dimethylcyclohexanone, and the like.

Examples of first protected (2E)-1-(4-chlorophenyl)-2-(hydroxymethylene)-4,4-dimethylcyclohexanols useful for the practice of this invention include (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, (2E)-2-(((tert-butyl(dimethyl)silyl)oxy)methylene)-1-(4-chlorophenyl)-4,4-dimethylcyclohexanol and the like.

Examples of first acids useful for the practice of this invention are tetra-n-butylammonium fluoride, trifluoroacetic acid, hydrochloric acid, trifluoromethanesulfonic acid, sulfuric acid and the like.

Step (a) is typically conducted for about 6 to about 18 hours in a solvent such as tetrahydrofuran, N,N-dimethylformamide, mixtures thereof and the like.

Step (b) is typically conducted for about 4 to about 16 hours in solvents such as tetrahydrofuran, DMF, toluene, 2-methyltetrahydrofuran, ethyl acetate, mixtures thereof and the like.

Step (c) is typically conducted from about 2 to about 4 hours in a solvent including toluene, diethyl ether, tetrahydrofuran, N,N-dimethylformamide and the like or mixtures thereof.

Step (d) is typically conducted from about 1 to about 4 hours in solvents such as toluene, diethyl ether, tetrahydrofuran, N,N-dimethylformamide, water, methanol, and the like or mixtures thereof.

Still another embodiment pertains to a process for making ethyl 4-(4-((2-(4-chlorophenyl)-5,5-/dimethylcyclohex-1-en-1-yl)methyl)piperazin-1-yl)benzoate, comprising:

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate.

Examples of first reducing agents useful for the practice of this invention include sodium triacetoxyborohydride and sodium cyanoborohydride.

Step (e) is typically conducted from about 10 to about 16 hours in solvents such as dichloromethane, acetonitrile, toluene, diethyl ether, tetrahydrofuran, N,N-dimethylformamide, methyl tert-butyl ether, mixtures thereof and the like.

Still another embodiment pertains to ethyl 4-(4-((2-(4-chlorophenyl)-5,5-dimethylcyclohex-1-en-1-yl)methyl)piperazin-1-yl)benzoate prepared as described in the preceding embodiment.

Still another embodiment pertains to ethyl 4-(4-((2-(4-chlorophenyl)-5,5-dimethylcyclohex-1-en-1-yl)methyl)piperazin-1-yl)benzoate, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof.

Another embodiment pertains to ethyl 4-(4-((2-(4-chlorophenyl)-5,5-dimethylcyclohex-1-en-1-yl)methyl)piperazin-1-yl)benzoate, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Still another embodiment pertains to a process for making 4-(4-((2-(4-chlorophenyl)-5,5-dimethylcyclohex-1-en-1-yl)methyl)piperazin-1-yl)benzoic acid, comprising:

(f) reacting ethyl 4-(4-((2-(4-chlorophenyl)-5,5-dimethylcyclohex-1-en-1-yl)methyl)piperazin-1-yl)benzoate and a third base and isolating or not isolating the 4-(4-((2-(4-chlorophenyl)-5,5-dimethylcyclohex-1-en-1-yl)methyl)piperazin-1-yl)benzoic acid.

Examples of third bases useful for the practice of this invention are sodium hydroxide, potassium hydroxide and the like.

Step (f) is typically conducted from about 10 hours to about 20 hours in solvents such as ethanol, tetrahydrofuran, heptanes, 2-methyltetrahydrofuran, water, mixtures thereof and the like.

Still another embodiment pertains to 4-(4-((2-(4-chlorophenyl)-5,5-dimethylcyclohex-1-en-1-yl)methyl)piperazin-1-yl)benzoic acid, or a pharmaceutically acceptable salt thereof, prepared as described in the preceding embodiment.

Still another embodiment pertains to 4-(4-((2-(4-chlorophenyl)-5,5-dimethylcyclohex-1-en-1-yl)methyl)piperazin-1-yl)benzoic acid, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof.

Another embodiment pertains to 4-(4-((2-(4-chlorophenyl)-5,5-dimethylcyclohex-1-en-1-yl)methyl)piperazin-1-yl)benzoic acid, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Still another embodiment of this invention, therefore, pertains to a process for making (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone; and (b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone.

Another embodiment pertains to (2E)-4,4-dimethyl-2-(((triisopropylsilyl)oxy)methylene)cyclohexanone, (2E)-4,4-dimethyl-2-(((trimethylsilyl)oxy)methylene)cyclohexanone, and 2E)-2-(((tert-butyl(dimethyl)silyl)oxy)methylene)-4,4-dimethylcyclohexanone, or a pharmaceutically acceptable salt thereof, prepared as described in the preceding embodiment.

Still another embodiment of this invention pertains to a process for making 2-(4-chlorophenyl)-5,5-dimethylcyclohex-1-ene-1-carbaldehyde, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and (d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Still another embodiment pertains to 2-(4-chlorophenyl)-5,5-dimethylcyclohex-1-ene-1-carbaldehyde, or a pharmaceutically acceptable salt thereof, prepared as described in the preceding embodiment.

Still another embodiment pertains to a process for making ethyl 4-(4-((2-(4-chlorophenyl)-5,5-dimethylcyclohex-1-en-1-yl)methyl)piperazin-1-yl)benzoate, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate.

Still another embodiment pertains to ethyl 4-(4-((2-(4-chlorophenyl)-5,5-dimethylcyclohex-1-en-1-yl)methyl)piperazin-1-yl)benzoate, or a pharmaceutically acceptable salt thereof, prepared as described in the preceding embodiment.

Still another embodiment pertains to a process for making 4-(4-((2-(4-chlorophenyl)-5,5-dimethylcyclohex-1-en-1-yl)methyl)piperazin-1-yl)benzoic acid, comprising:

(f) reacting ethyl 4-(4-((2-(4-chlorophenyl)-5,5-dimethylcyclohex-1-en-1-yl)methyl)piperazin-1-yl)benzoate and sodium hydroxide and isolating or not isolating the 4-(4-((2-(4-chlorophenyl)-5,5-dimethylcyclohex-1-en-1-yl)methyl)piperazin-1-yl)benzoic acid.

Still another embodiment pertains to 4-(4-((2-(4-chlorophenyl)-5,5-dimethylcyclohex-1-en-1-yl)methyl)piperazin-1-yl)benzoic acid, or a pharmaceutically acceptable salt thereof, prepared as described in the preceding embodiment.

Still another embodiment of this invention, therefore, pertains to a process for making (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone, comprising:

(a) reacting 4,4-dimethylcyclohexanone, ethyl formate and potassium tert-butoxide to provide (2E)-2-(hydroxymethylene)-4,4-dimethylcyclohexanone at about −10° C. to about 0° C. and isolating or not isolating the (2E)-2-(hydroxymethylene)-4,4-dimethylcyclohexanone; and (b) reacting the (2E)-2-(hydroxymethylene)-4,4-dimethylcyclohexanone, triethylamine and trimethylchlorosilane, tert-butylchlorodimethylsilane, or triisopropylchlorosilane at about −10° C. to about 0° C. to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone.

Another embodiment pertains to (2E)-4,4-dimethyl-2-(((triisopropylsilyl)oxy)methylene)cyclohexanone, (2E)-4,4-dimethyl-2-(((trimethylsilyl)oxy)methylene)cyclohexanone, and 2E)-2-(((tert-butyl(dimethyl)silyl)oxy)methylene)-4,4-dimethylcyclohexanone, or a pharmaceutically acceptable salt thereof, prepared as described in the preceding embodiment.

Still another embodiment pertains to a process for making 2-(4-chlorophenyl)-5,5-dimethylcyclohex-1-ene-1-carbaldehyde, comprising:

(a) reacting 4,4-dimethylcyclohexanone, ethyl formate and potassium tert-butoxide at about −10° C. to about 0° C. to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane at about −10° C. to about 0° C. to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide at about −10° C. to about 5° C. to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol, and (d) reacting ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl) oxy)methylene)-1-(4-chlorophenyl)-4,4-dimethylcyclohexanol and hydrochloric acid at about 5° C. to about 20° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Still another embodiment pertains to 2-(4-chlorophenyl)-5,5-dimethylcyclohex-1-ene-1-carbaldehyde, or a pharmaceutically acceptable salt thereof, prepared as described in the preceding embodiment.

Still another embodiment pertains to a process for making ethyl 4-(4-((2-(4-chlorophenyl)-5,5-dimethylcyclohex-1-en-1-yl)methyl)piperazin-1-yl)benzoate, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate.

Still another embodiment pertains to ethyl 4-(4-((2-(4-chlorophenyl)-5,5-dimethylcyclohex-1-en-1-yl)methyl)piperazin-1-yl)benzoate, or a pharmaceutically acceptable salt thereof, prepared as described in the preceding embodiment.

Still another embodiment pertains to a process for making 4-(4-((2-(4-chlorophenyl)-5,5-dimethylcyclohex-1-en-1-yl)methyl)piperazin-1-yl)benzoic acid, comprising:

(f) reacting ethyl 4-(4-((2-(4-chlorophenyl)-5,5-dimethylcyclohex-1-en-1-yl)methyl)piperazin-1-yl)benzoate and sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid.

Still another embodiment pertains to 4-(4-((2-(4-chlorophenyl)-5,5-dimethylcyclohex-1-en-1-yl)methyl)piperazin-1-yl)benzoic acid, or a pharmaceutically acceptable salt thereof, prepared as described in the preceding embodiment.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide comprising:

(g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide and a first coupling reagent with or without a fourth base and with or without an auxiliary coupling reagent, and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide, or a pharmaceutically acceptable salt thereof, prepared as described in the preceding embodiment.

Still another embodiment pertains to a process for making an apoptosis promoter, or a pharmaceutically acceptable salt thereof, such as those described in, for example, U.S. Patent Publication US2005/0159427A1, the '799 Patent, and U.S. Provisional Applications 61/145611, 61/120275, 61/181180, and 61/181203, comprising:

(g) reacting 4-(4-((2-(4-chlorophenyl)-5,5-dimethylcyclohex-1-en-1-yl)methyl)piperazin-1-yl)benzoic acid, a first appropriate benzenesulfonamide and a first coupling reagent with or without a fourth base and with or without an auxiliary coupling reagent, and isolating or not isolating the apoptosis promoter.

Examples of first coupling reagents are 1-ethyl-3-(3-(dimethylamino)propyl)-carbodiimide hydrochloride, N,N'-dicyclohexylcarbodiimide, N,N'-diisopropylcarbodiimide, 1,1'-carbonyldiimidazole and the like.

Examples of first auxiliary coupling reagents include 4-dimethylaminopyridine, hydroxybenzotriazole, 1-hydroxy-7-aza-benzotriazole and the like.

Examples of fourth bases include 1,8-diazabicyclo(5.4.0)undec-7-ene, potassium tert-butoxide and the like.

Examples of apoptosis promoters include 4-(4-((2-(4-chlorophenyl)-5,5-dimethylcyclohex-1-en-1-yl)methyl)piperazin-1-yl)-N-((4-(((1R)-3-(dimethylamino)-1-((phenylthio)methyl)propyl)amino)-3-nitrophenyl)sulfonyl)benzamide, 4-(4-((2-(4-chlorophenyl)-5,5-dimethylcyclohex-1-en-1-yl)methyl)piperazin-1-yl)-N-((4-(((1R)-3-(isopropyl(methyl)amino)-1-((phenylthio)methyl)propyl)amino)-3-((trifluoromethyl)sulfonyl)phenyl)sulfonyl)benzamide, 4-(4-((2-(4-chlorophenyl)-5,5-dimethylcyclohex-1-en-1-yl)methyl)piperazin-1-yl)-N-((5-(((1R)-3-(isopropyl(methyl)amino)-1-((phenylthio)methyl)propyl)amino)-4-nitrothien-2-yl)sulfonyl)benzamide, 4-(4-((2-(4-chlorophenyl)-5,5-dimethylcyclohex-1-en-1-yl)methyl)piperazin-1-yl)-N-((4-((3-morpholin-4-ylpropyl)amino)-3-nitrophenyl)sulfonyl)-2-phenoxybenzamide, 4-(4-((2-(4-chlorophenyl)-5,5-dimethylcyclohex-1-en-1-yl)methyl)piperazin-1-yl)-N-((3-nitro-4-((tetrahydro-2H-pyran-4-ylmethyl)amino)phenyl)sulfonyl)-2-(1H-pyrrolo(2,3-b)pyridin-5-yloxy)benzamide, and the like.

Examples of first appropriate benzenesulfonamides include 4-(((1R)-3-morpholin-4-yl-1-((phenylthio)methyl)propyl)amino)-3-((trifluoromethyl)sulfonyl)benzenesulfonamide, (R)-4-(4-(dimethylamino)-1-(phenylthio)butan-2-ylamino)-3-nitrobenzenesulfonamide, and the like.

Step (g) is typically conducted from about 36 to about 50 hours in solvents such as dichloromethane, acetonitrile, dioxane, tetrahydrofuran, mixtures thereof and the like.

Still another embodiment pertains to a process for making an apoptosis promoter, or a pharmaceutically acceptable salt thereof, compounds such as those described in, for example, U.S. Patent Publication US2005/0159427A1, the '799 Patent, and U.S. Provisional Applications 61/145611, 61/120275, 61/181180, and 61/181203, comprising:

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, a first appropriate benzenesulfonamide and a first coupling reagent with or without a fourth base and with or without an auxiliary coupling reagent, and isolating or not isolating the apoptosis promoter.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide and a first coupling reagent with or without a fourth base and with or without an auxiliary coupling reagent, and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide comprising:

(g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment pertains to a process for making an apoptosis promoter, or a pharmaceutically acceptable salt thereof, such as those described in, for example, U.S. Patent Publication US2005/0159427A1, the '799 Patent, and U.S. Provisional Applications 61/145611, 61/120275, 61/181180, and 61/181203, comprising:

(g) reacting 4-(4-((2-(4-chlorophenyl)-5,5-dimethylcyclohex-1-en-1-yl)methyl)piperazin-1-yl)benzoic acid, a first appropriate amine, 1-ethyl-3-(3-(dimethylamino)propyl)carbodiimide hydrochloride and 4-dimethylaminopyridine, and isolating or not isolating the apoptosis promoter.

Still another embodiment pertains to a process for making an apoptosis promoter, or a pharmaceutically acceptable salt thereof, for use in making compounds, such as those described in, for example, U.S. Patent Publication US2005/

0159427A1, the '799 Patent, and U.S. Provisional Applications 61/145611, 61/120275, 61/181180, and 61/181203, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, a first appropriate amine, 1-ethyl-3-(3-(dimethylamino)propyl)carbodiimide hydrochloride and 4-dimethylaminopyridine, and isolating or not isolating the apoptosis promoter.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide comprising:

(g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment pertains to a process for making an apoptosis promoter, or a pharmaceutically acceptable salt thereof, such as those described in, for example, U.S. Patent Publication US2005/0159427A1, the '799 Patent, and U.S. Provisional Applications 61/145611, 61/120275, 61/181180, and 61/181203, comprising:

(g) reacting 4-(4-((2-(4-chlorophenyl)-5,5-dimethylcyclohex-1-en-1-yl)methyl)piperazin-1-yl)benzoic acid, a first appropriate amine, 1-ethyl-3-(3-(dimethylamino)propyl)carbodiimide hydrochloride and 4-dimethylaminopyridine at about 25° C. to about 35° C., and isolating or not isolating the apoptosis promoter.

Still another embodiment pertains to a process for making an apoptosis promoter, or a pharmaceutically acceptable salt thereof, such as those described in, for example, U.S. Patent Publication US2005/0159427A1, the '799 Patent, and U.S. Provisional Applications 61/145611, 61/120275, 61/181180, and 61/181203, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, a first appropriate amine, 1-ethyl-3-(3-(dimethylamino)propyl)carbodiimide hydrochloride and 4-dimethylaminopyridine at about 25° C. to about 35° C., and isolating or not isolating the apoptosis promoter.

Still another embodiment pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(a) reacting 4,4-dimethylcyclohexanone, ethyl formate and potassium tert-butoxide at about −10° C. to about 0° C. to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane at about −10° C. to about 0° C. to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide at about −10° C. to about 5° C. to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol, and (d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid at about 5° C. to about 20° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

One embodiment of this invention, therefore, pertains to a process for making 2-(4-chlorophenyl)-5,5-dimethylcyclohex-1-ene-1-carbaldehyde, comprising:

(h) reacting 4,4-dimethylcyclohexanone, diethoxycarbenium fluoroborate and a fifth base to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol; and (j) reacting the 1-(4-chlorophenyl)-2-(diethoxymethyl)-4,4-dimethylcyclohexanol and a second acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Another embodiment pertains to 2-(4-chlorophenyl)-5,5-dimethylcyclohex-1-ene-1-carbaldehyde, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof.

Another embodiment pertains to 2-(4-chlorophenyl)-5,5-dimethylcyclohex-1-ene-1-carbaldehyde, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Examples of fifth bases useful for the practice of this invention include N,N-diisopropylethylamine, 1,8-diazabicyclo(5.4.0)undec-7-ene and the like.

Examples of second acids useful for the practice of this invention include aqueous hydrochloric acid, sulfuric acid and the like.

Step (h) is typically conducted for about 1 to about 3 hours in a solvent such as dichloromethane and the like.

Step (i) is typically conducted for about 1 to about 3 hours in a solvent such as tetrahydrofuran, diethyl ether, mixtures thereof and the like.

Step (j) is typically conducted for about 15 to about 20 hours in a solvent such as tetrahydrofuran, diethyl ether, mixtures thereof and the like.

Still another embodiment of this invention, therefore, pertains to a process for making 2-(4-chlorophenyl)-5,5-dimethylcyclohex-1-ene-1-carbaldehyde, comprising:

(h) reacting 4,4-dimethylcyclohexanone, diethoxycarbenium fluoroborate and N,N-diisopropylethylamine to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol; and (j) reacting the 1-(4-chlorophenyl)-2-(diethoxymethyl)-4,4-dimethylcyclohexanol and aqueous hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Still another embodiment of this invention, therefore, pertains to a process for making 2-(4-chlorophenyl)-5,5-dimethylcyclohex-1-ene-1-carbaldehyde, comprising:

(h) reacting 4,4-dimethylcyclohexanone, diethoxycarbenium fluoroborate and N,N-diisopropylethylamine at about −60° C. to −90° C. to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide at about −60° C. to −10° C. to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol; and (j) reacting the 1-(4-chlorophenyl)-2-(diethoxymethyl)-4,4-dimethylcyclohexanol and aqueous hydrochloric acid at about 50° C. to 80° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(h) reacting 4,4-dimethylcyclohexanone, diethoxycarbenium fluoroborate and a fifth base to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol;

(j) reacting the 1-(4-chlorophenyl)-2-(diethoxymethyl)-4,4-dimethylcyclohexanol and a second acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(h) reacting 4,4-dimethylcyclohexanone, diethoxycarbenium fluoroborate and N,N-diisopropylethylamine to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol;

(j) reacting the 1-(4-chlorophenyl)-2-(diethoxymethyl)-4,4-dimethylcyclohexanol and aqueous hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-

3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(h) reacting 4,4-dimethylcyclohexanone, diethoxycarbenium fluoroborate and N,N-diisopropylethylamine at about −60° C. to −90° C. to provide (2-(diethoxymethyl)-4,4-dimethylcyclohexanone and isolating or not isolating the 2-(diethoxymethyl)-4,4-dimethylcyclohexanone;

(i) reacting the 2-(diethoxymethyl)-4,4-dimethylcyclohexanone and 4-chlorophenyl magnesium bromide at about −60° C. to −10° C. to provide 1-(4-chlorophenyl)-2-(diethoxymethyl)-4,4-dimethylcyclohexanol and isolating or not isolating the 1-(4-chlorophenyl)-2-(diethoxymethyl)-4,4-dimethylcyclohexanol;

(j) reacting the 1-(4-chlorophenyl)-2-(diethoxymethyl)-4,4-dimethylcyclohexanol and aqueous hydrochloric acid at about 50° C. to 80° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

One embodiment of this invention, therefore, pertains to a process for making 2-(4-chlorophenyl)-5,5-dimethylcyclohex-1-ene-1-carbaldehyde, comprising:

(k) reacting 4,4-dimethylcyclohexanone, and phosphorus oxychloride to provide 2-chloro-5,5-dimethylcyclohex-1-enecarbaldehyde and isolating or not isolating the 2-chloro-5,5-dimethylcyclohex-1-enecarbaldehyde; and (l) reacting the 2-chloro-5,5-dimethylcyclohex-1-enecarbaldehyde, 4-chlorophenylboronic acid, a first phase transfer catalyst, a fifth base, and a first palladium catalyst to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Another embodiment pertains to 2-(4-chlorophenyl)-5,5-dimethylcyclohex-1-ene-1-carbaldehyde, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof.

Another embodiment pertains to 2-(4-chlorophenyl)-5,5-dimethylcyclohex-1-ene-1-carbaldehyde, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Examples of first phase transfer catalysts useful for the practice of this invention include tetrabutyl ammonium bromide, tetrapropyl ammonium bromide, tributyl benzyl ammonium chloride, tetraethyl ammonium bromide, tetraoctyl ammonium bromide, tetra butyl ammonium hydrogen sulphate, benzyl trimethyl ammonium chloride, benzyl triethyl ammonium chloride, tetrabutyl ammonium acetate, tetrabutyl ammonium iodide, and the like.

Examples of fifth bases useful for the practice of this invention include potassium carbonate, potassium phosphate, potassium fluoride, potassium t-butoxide and the like.

Examples of first palladium catalysts useful for the practice of this invention include palladium (II) acetate, tris(dibenzylideneacetone)dipalladium(0), tetrakis(triphenylphosphine)palladium(0), (1,1'-bis(diphenylphosphino)ferrocene)dichloropalladium(II), and the like.

Step (k) is typically conducted for about 15 to about 20 hours in a solvent such as dichloromethane, N,N-dimethylformamide, mixtures thereof and the like.

Step (l) is typically conducted for about 5 to about 10 hours in a solvent such as water, or mixtures of water and one or more organic solvents such as toluene, methylene chloride, DMF, and the like.

Another embodiment of this invention, therefore, pertains to a process for making 2-(4-chlorophenyl)-5,5-dimethylcyclohex-1-ene-1-carbaldehyde, comprising:

(k) reacting 4,4-dimethylcyclohexanone, and phosphorus oxychloride to provide 2-chloro-5,5-dimethylcyclohex-1-enecarbaldehyde and isolating or not isolating the 2-chloro-5,5-dimethylcyclohex-1-enecarbaldehyde; and (l) reacting the 2-chloro-5,5-dimethylcyclohex-1-enecarbaldehyde, 4-chlorophenylboronic acid, tetrabutyl ammonium bromide, potassium carbonate, and palladium (II) acetate to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Another embodiment of this invention, therefore, pertains to a process for making 2-(4-chlorophenyl)-5,5-dimethylcyclohex-1-ene-1-carbaldehyde, comprising:

(k) reacting 4,4-dimethylcyclohexanone and phosphorus oxychloride at about 20° C. to 45° C. to provide 2-chloro-5,5-dimethylcyclohex-1-enecarbaldehyde and isolating or not isolating the 2-chloro-5,5-dimethylcyclohex-1-enecarbaldehyde; and (l) reacting the 2-chloro-5,5-dimethylcyclohex-1-enecarbaldehyde, 4-chlorophenylboronic acid, tetrabutyl ammonium bromide, potassium carbonate, and palladium (II) acetate at about 20° C. to 45° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde.

Another embodiment pertains to 2-(4-chlorophenyl)-5,5-dimethylcyclohex-1-ene-1-carbaldehyde, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(k) reacting 4,4-dimethylcyclohexanone, and phosphorus oxychloride to provide 2-chloro-5,5-dimethylcyclohex-1-enecarbaldehyde and isolating or not isolating the 2-chloro-5,5-dimethylcyclohex-1-enecarbaldehyde;

(l) reacting the 2-chloro-5,5-dimethylcyclohex-1-enecarbaldehyde, 4-chlorophenylboronic acid, a first phase transfer catalyst, a fifth base, and a first palladium catalyst to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(k) reacting 4,4-dimethylcyclohexanone, and phosphorus oxychloride to provide 2-chloro-5,5-dimethylcyclohex-1-enecarbaldehyde and isolating or not isolating the 2-chloro-5,5-dimethylcyclohex-1-enecarbaldehyde;

(l) reacting the 2-chloro-5,5-dimethylcyclohex-1-enecarbaldehyde, 4-chlorophenylboronic acid, tetrabutyl ammonium bromide, potassium carbonate, and palladium (II) acetate to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(k) reacting 4,4-dimethylcyclohexanone and phosphorus oxychloride at about 20° C. to 45° C. to provide 2-chloro-5,5-dimethylcyclohex-1-enecarbaldehyde and isolating or not isolating the 2-chloro-5,5-dimethylcyclohex-1-enecarbaldehyde;

(l) reacting the 2-chloro-5,5-dimethylcyclohex-1-enecarbaldehyde, 4-chlorophenylboronic acid, tetrabutyl ammonium bromide, potassium carbonate, and palladium (II) acetate at about 20° C. to 45° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide, or a pharmaceutically acceptable salt thereof, prepared as described in the preceding embodiment.

One embodiment of this invention, therefore, pertains to a process for making 4-(((1R)-3-morpholin-4-yl-1-((phenylthio)methyl)propyl)amino)-3-((trifluoromethyl)sulfonyl) benzenesulfonamide, comprising:

(m) reacting 2-fluorobenzenesulfonyl chloride, and a first fluoride source to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and a second fluoride source to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide or a salt thereof.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Examples of first fluoride sources useful for the practice of this invention include tetra-n-butylammonium fluoride and potassium fluoride, and mixtures thereof.

Examples of second fluoride sources useful for the practice of this invention include tris(dimethylamino)sulfonium difluorotrimethylsilicate, tetra-n-butylammonium fluoride, cesium fluoride, tetrabutylammonium triphenyldifluorosilicate, and tetrabutylammonium triphenyldifluorsilicate.

Examples of first $NH_3$ sources useful for the practice of this invention include aqueous ammonium hydroxide, ammonia in methanol, ammonium carbamate, ammonia in isopropyl alcohol, and hexamethyldisilazane.

Examples of sixth bases useful for the practice of this invention include triethylamine and the like.

Step (m) is typically conducted for about 30 minutes to about 2 hours in a solvent such as tetrahydrofuran, acetonitrile, water, mixtures thereof and the like.

Step (n) is typically conducted for about 30 minutes to about 2 hours in a solvent such as dichloromethane, tetrahydrofuran, toluene, dimethoxyethane, N-methyl-2-pyrrolidone mixtures thereof and the like.

Step (o) is typically conducted for about 15 to about 25 hours.

Step (p) is typically conducted for about 30 minutes to about 24 hours in a solvent such acetonitrile, tetrahydrofuran, ethyl acetate, isopropyl alcohol, isopropyl acetate, dimethoxyethane, dichloromethane, toluene, mixtures thereof and the like.

Step (q) is typically conducted for about 12 to about 24 hours in a solvent such as ethyl acetate, tetrahydrofuran, 2-methyl tetrahydrofuran, mixtures thereof and the like.

Another embodiment of this invention pertains to a process for making 4-(((1R)-3-morpholin-4-yl-1-((phenylthio)methyl)propyl)amino)-3-((trifluoromethyl)sulfonyl)benzenesulfonamide, comprising:

(m) reacting 2-fluorobenzenesulfonyl chloride, and tetra-n-butylammonium fluoride to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Another embodiment of this invention pertains to a process for making 4-(((1R)-3-morpholin-4-yl-1-((phenylthio)methyl)propyl)amino)-3-((trifluoromethyl)sulfonyl)benzenesulfonamide, comprising:

(m) reacting 2-fluorobenzenesulfonyl chloride, and tetra-n-butylammonium fluoride at about −10° C. to about 10° C. to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate at about room temperature to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(m) reacting 2-fluorobenzenesulfonyl chloride, and a first fluoride source to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and a second fluoride source to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(m) reacting 2-fluorobenzenesulfonyl chloride, and tetra-n-butylammonium fluoride to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(m) reacting 2-fluorobenzenesulfonyl chloride, and tetra-n-butylammonium fluoride at about 0° C. to about 10° C. to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate at about room temperature to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

One embodiment of this invention, therefore, pertains to a process for making 4-(((1R)-3-morpholin-4-yl-1-((phenylthio)methyl)propyl)amino)-3-((trifluoromethyl)sulfonyl)benzenesulfonamide, comprising:

(r) reacting a first metal trifluoromethanesulfinate, a first aryl fluoride, and a first catalyst to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Another embodiment pertains to 4-(((1R)-3-morpholin-4-yl-1-((phenylthio)methyl)propyl)amino)-3-((trifluoromethyl)sulfonyl)benzenesulfonamide for use in making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, for use in making compounds such as those described in, for example, U.S. Patent Publication US2005/0159427A1, the '799 Patent, and U.S. Provisional Applications 61/145611, 61/120275, 61/181180, and 61/181203.

Examples of first catalysts useful for the practice of this invention include CuI, $Cu_2O$, CuCl, copper (I) trifluoromethanesulfonate benzene complex, copper triflate, CuSCN, copper acetate, and palladium(II) acetate alone or in combination with ligands such as tetramethylethylenediamine, 4,4'-ditert-butyl-2,2'-dipyridyl, 1,10-phenanthroline, 2,9-dimethyl-1,10-phenanthroline, 3,4,7,8-tetramethyl-1,10-phenanthroline, 4,7-diphenyl-1,10-phenanthrolines, 2-acetylcyclohexanone, N,N-diethylsalicylamide, triphenyl phosphine, tri-tert-butylphosphine, 2,2'-bis(diphenylphosphino)-

1,1'-binaphthyl, 1,1'-bis(diphenylphosphino)ferrocene, 2-(di-t-butylphosphino)biphenyl, triphenyl phosphite, triphenylphosphine oxide, dimethylmethylphosphonate, 1,3-bis (2,4,6-trimethylphenyl)-1,3-dihydro-2H-imidazol-2-ylidene, 1,3-bis(2,6-diisopropylphenyl)-imidazol-2-ylidene, 1,3-bis(1-adamantyl)imidazol-2-ylidene, 1,3-di-tert-butyl-imidazol-2-ylidene and the like.

Examples of first metal trifluoromethanesulfinates useful for the practice of this invention include potassium trifluoromethanesulfinate, lithium trifluoromethanesulfinate, rubidium trifluoromethanesulfinate, cesium trifluoromethanesulfinate, and the like.

Examples of first aryl fluoride sources useful for the practice of this invention include mesityl-2-fluorophenyl iodonium triflate, bis-(2-fluorophenyl)iodonium alkyl-sulfonates, bis-(2-fluorophenyl)iodonium aryl-sulfonates, bis-(2-fluorophenyl)iodonium cycloalkyl-sulfonates, bis-(2-fluorophenyl)iodonium heterocycle-sulfonates, bis-(2-fluorophenyl) iodonium tetrafluoroborates, bis-(2-fluorophenyl)iodonium hexafluorophosphates, and the like.

Step (r) is typically conducted for about 10 hours to about 20 hours in a solvent such as N,N-dimethylformamide, dimethylsulfoxide, dimethylacetamide, 1,4-dioxane, 1,2-dimethoxyethane, tetrahydrofuran, 1-methyl-2-pyrrolidinone, diglyme, methyl tert-butyl ether, methylene dichloride, chloroform, carbon tetrachloride, acetone, ethyl acetate, isopropyl acetate, acetonitrile, benzonitrile, toluene, benzene, mesitylene, xylenes, anisole, chlorobenzenes, fluorobenzenes, hexanes, heptanes, pentanes, methanol, ethanol, propanol, butanol, tert-butanol, hexanol, octanol, pyridines, tributylamines, mixtures thereof and the like.

Another embodiment of this invention pertains to a process for making 4-(((1R)-3-morpholin-4-yl-1-((phenylthio)methyl)propyl)amino)-3-((trifluoromethyl)sulfonyl)benzenesulfonamide, comprising:

(r) reacting sodium trifluoromethanesulfinate, bis-(2-fluorophenyl)iodonium tetrafluoroborate and copper(I) oxide to provide 1-fluoro-2-((trifluoromethyl)sulfonyl)benzene and isolating or not isolating the 1-fluoro-2-((trifluoromethyl) sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Another embodiment of this invention pertains to a process for making 4-(((1R)-3-morpholin-4-yl-1-((phenylthio)methyl)propyl)amino)-3-((trifluoromethyl)sulfonyl)benzenesulfonamide, comprising:

(r) reacting sodium trifluoromethanesulfinate, bis-(2-fluorophenyl)iodonium tetrafluoroborate and copper(I) oxide at about 0° C. to about 110° C. to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio) methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide.

Another embodiment pertains to 4-(((1R)-3-morpholin-4-yl-1-((phenylthio)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(r) reacting sodium trifluoromethanesulfinate, bis-(2-fluorophenyl)iodonium tetrafluoroborate and a first catalyst to provide 1-fluoro-2-((trifluoromethyl)sulfonyl)benzene and isolating or not isolating the 1-fluoro-2-((trifluoromethyl) sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(r) reacting sodium trifluoromethanesulfinate, bis-(2-fluorophenyl)iodonium tetrafluoroborate and copper(I) oxide to provide 1-fluoro-2-((trifluoromethyl)sulfonyl)benzene and isolating or not isolating the 1-fluoro-2-((trifluoromethyl) sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(r) reacting sodium trifluoromethanesulfinate, bis-(2-fluorophenyl)iodonium tetrafluoroborate and copper(I) oxide at about 0° C. to about 110° C. to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide; and (q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl) sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and a first fluoride source to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and a second fluoride source to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and (d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and tetra-n-butylammonium fluoride to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide at about −10° C. to about 0° C. to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane at about −10° C. to about 0° C. to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide at about −10° C. to about 5° C. to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol, and (d) reacting ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid at about 5° C. to about 20° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and tetra-n-butylammonium fluoride at about 0° C. to about 10° C. to provide 2-fluorobenzenesulfonyl fluoride and isolating or not isolating the 2-fluorobenzenesulfonyl fluoride;

(n) reacting the 2-fluorobenzenesulfonyl fluoride, Rupert's reagent ($CH_3SiCF_3$), and tris(dimethylamino)sulfonium difluorotrimethylsilicate at about room temperature to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)
benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(r) reacting sodium trifluoromethanesulfinate, bis-(2-fluorophenyl)iodonium tetrafluoroborate and a first catalyst to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and (d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid;

(r) reacting sodium trifluoromethanesulfinate, bis-(2-fluorophenyl)iodonium tetrafluoroborate and copper(I) oxide to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, prepared as described in the preceding embodiment.

Still another embodiment of this invention pertains to a process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide at about −10° C. to about 0° C. to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane at about −10° C. to about 0° C. to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide at about −10° C. to about 5° C. to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol, and (d) reacting ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid at about 5° C. to about 20° C. to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride at about 15° C. to about 30° C. and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide at about 55° C. to about 75° C., and isolating or not isolating the 4-(4-((2-(4-chlorophenyl)-5,5-dimethylcyclohex-1-en-1-yl)methyl)piperazin-1-yl)benzoic acid;

(r) reacting sodium trifluoromethanesulfinate, bis-(2-fluorophenyl)iodonium tetrafluoroborate and copper(I) oxide at about 0° C. to about 110° C. to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid at about 110° C. to about 130° C. to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide at about −5° C. to about −60° C. to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine at about 40° C. to about 50° C. to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine at about 25° C. to about 35° C. and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

Still another embodiment pertains to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)

sulfonyl)benzenesulfonamide, or a pharmaceutically acceptable salt thereof, prepared as described in the preceding embodiment.

The following schemes and examples are presented to provide what is believed to be the most useful and readily understood description of procedures and conceptual aspects of this invention.

Schemes nyl)-5,5-dimethylcyclohex-1-en-1-yl)methyl)piperazin-1-yl)benzoate, which is hydrolyzed to provide 4-(4-((2-(4-chlorophenyl)-5,5-dimethylcyclohex-1-en-1-yl)methyl)piperazin-1-yl)benzoic acid (6).

One such route involves reacting 4,4-dimethylcyclohexanone (1A) and an alkyl formate such as but not limited to ethyl formate, in the presence of a base such as but not limited to potassium t-butoxide to provide (2E)-2-(hydroxymethyl-

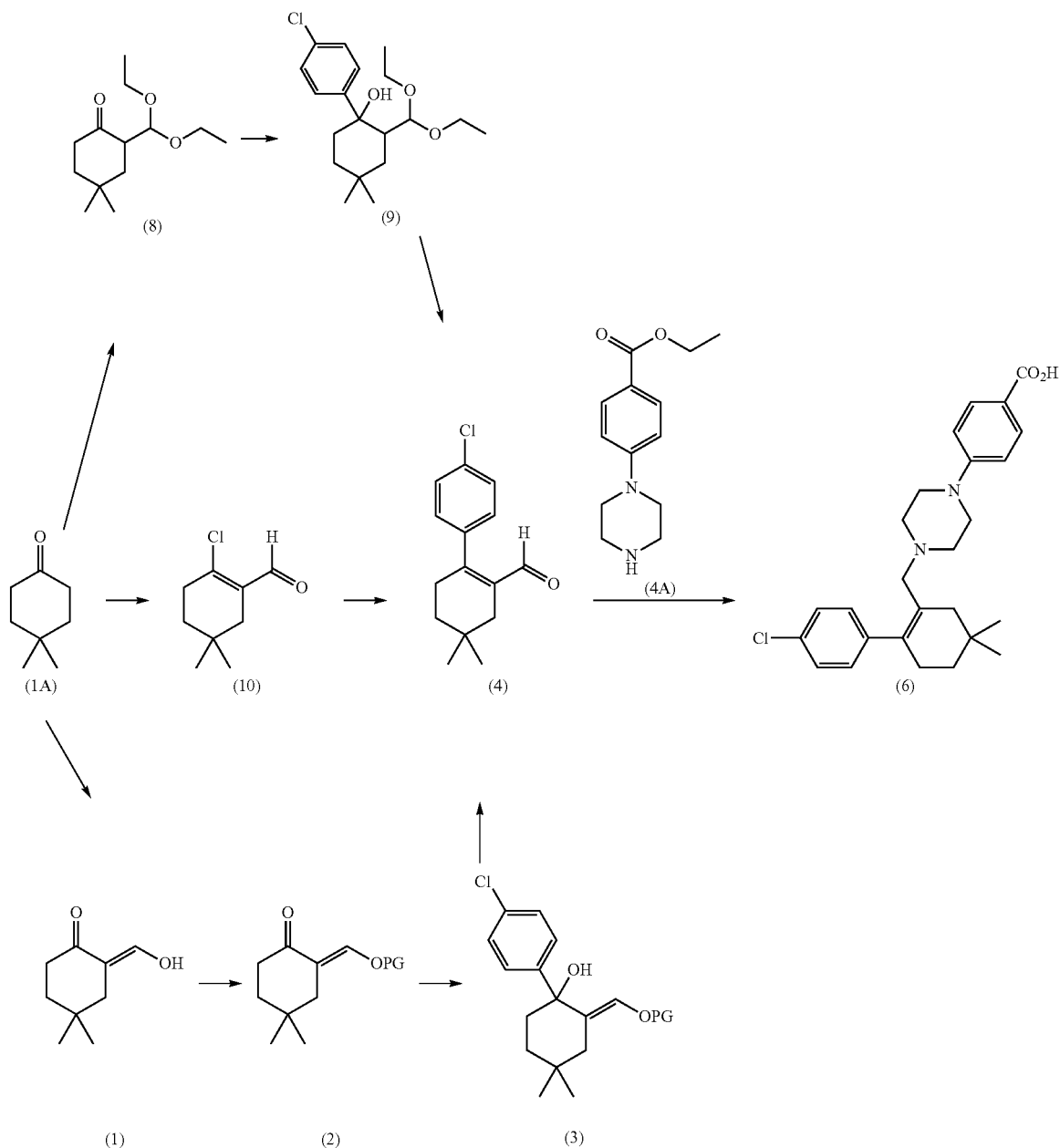

Scheme 1

Scheme 1 shows three synthetic routes used to prepare the aldehyde intermediate (2-(4-chlorophenyl)-5,5-dimethylcyclohex-1-ene-1-carbaldehyde) (4) from (2E)-2-(hydroxymethylene)-4,4-dimethylcyclohexanone (1A). The aldehyde intermediate (4) can then be reacted with ethyl 4-(piperazin-1-yl)benzoate (4A) to provide ethyl 4-(4-((2-(4-chlorophenyl)-ene)-4,4-dimethylcyclohexanone (1). The reaction is typically performed below room temperature in a solvent such as but not limited to tetrahydrofuran, before warming to room temperature and stirring overnight. (2E)-2-(Hydroxymethylene)-4,4-dimethylcyclohexanone (1) is then reacted with a base such as but not limited to triethylamine and a silyl ether protecting group reagent such as but not limited to triisopropylsilylchloride to provide the protected (2E)-2-(hydroxymethylene)-4,4-dimethylcyclohexanone (2). The reaction is typically performed below room temperature in a solvent such as but not limited to 2-methyltetrahydrofuran. (4-Chlorophenyl)magnesium bromide is then added to a solution of the protected alcohol (2) to provide the protected (2E)-1-(4-chlorophenyl)-2-(hydroxymethylene)-4,4-dimethylcyclohexanol (3). The reaction is typically performed below room temperature in a solvent such as but not limited to tetrahydrofuran, toluene, or mixtures thereof. The protected (2E)-1-(4-chlorophenyl)-2-(hydroxymethylene)-4,4-dimethylcyclohexanol (3) can be treated with an acid such as but not limited to HCl, to provide the aldehyde intermediate (2-(4-chlorophenyl)-5,5-dimethylcyclohex-1-ene-1-carbaldehyde) (4).

Another route involves reacting dimethylcyclohexanone (1A) with a prepared solution of diethoxycarbenium fluoroborate to provide 2-(diethoxymethyl)-4,4-dimethylcyclohexanone (8). The reaction is typically performed below room temperature in a solvent such as but not limited to methylene chloride. Chlorophenyl magnesium bromide is then added to a solution of 2-(diethoxymethyl)-4,4-dimethylcyclohexanone (8) to provide 1-(4-chlorophenyl)-2-(diethoxymethyl)-4,4-dimethylcyclohexanol (9). The reaction is typically performed below room temperature in a solvent such as but not limited to tetrahydrofuran. 1-(4-Chlorophenyl)-2-(diethoxymethyl)-4,4-dimethylcyclohexanol (9) can be treated with an acid such as but not limited to HCl, to provide the aldehyde intermediate (2-(4-chlorophenyl)-5,5-dimethylcyclohex-1-ene-1-carbaldehyde) (4).

Still another route involves reacting dimethylcyclohexanone (1A) with POCl$_3$ to provide 2-chloro-5,5-dimethylcyclohex-1-enecarbaldehyde (10). The reaction is typically performed below room temperature in a solvent such as but not limited to methylene chloride, N,N-dimethylformamide, or mixtures thereof. The aldehyde intermediate (2-(4-chlorophenyl)-5,5-dimethylcyclohex-1-ene-1-carbaldehyde) (4) can be prepared from 2-chloro-5,5-dimethylcyclohex-1-enecarbaldehyde (10) by reacting the latter with 4-chlorophenylboronic acid, a phase transfer catalyst such as but not limited to tetrabutyl ammonium bromide, a palladium catalyst such as but not limited to palladium (II) acetate in the presence of a base such as but not limited to K$_2$CO$_3$. The reaction is typically performed above room temperature in a solvent such as but not limited to water.

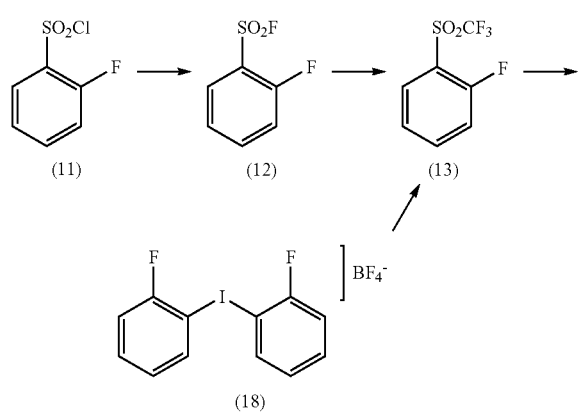

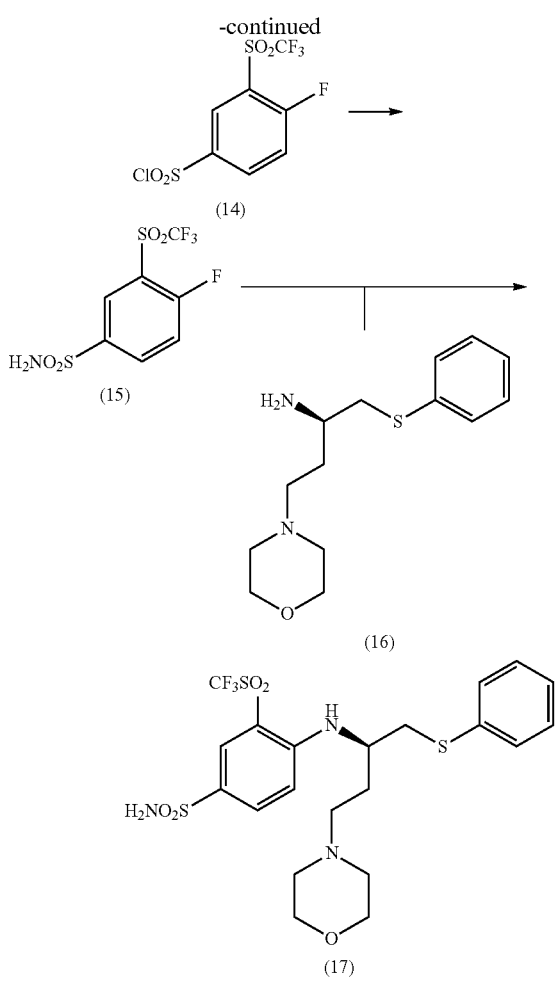

Scheme 2 shows two routes used to make 4-(((1R)-3-morpholin-4-yl-1-((phenylthio)methyl)propyl)amino)-3-((trifluoromethyl)sulfonyl)benzenesulfonamide (17). One route involves reacting commercially available 2-fluorobenzenesulfonyl chloride (11) with TBAF (tetra-n-butylammonium fluoride) to provide 2-fluorobenzenesulfonyl fluoride (12). The reaction is typically performed below room temperature in a solvent such as but not limited to tetrahydrofuran. 2-Fluorobenzenesulfonyl fluoride (12) can be converted to 1-fluoro-2-((trifluoromethyl)sulfonyl)benzene (13) by reaction with Ruppert's reagent (CH$_3$SiCF$_3$) catalyzed by (((CH$_3$)$_2$N)$_3$S)$^+$ (F$_2$Si(CH$_3$)$_3$)$^-$, also known as TASF. The reaction is typically performed at about room temperature in a solvent such as but not limited to tetrahydrofuran, dichloromethane, toluene, dimethoxyethane, or mixtures thereof. 1-Fluoro-2-((trifluoromethyl)sulfonyl)benzene (13) can be reacted with chlorosulfonic acid to provide 4-fluoro-3-((trifluoromethyl)sulfonyl)benzenesulfonyl chloride (14). The reaction is typically performed at an elevated temperature before cooling for the addition of SO$_2$Cl$_2$, used to quench the chlorosulfonic acid. 4-Fluoro-3-((trifluoromethyl)sulfonyl)benzenesulfonamide (15) can be prepared from 4-fluoro-3-((trifluoromethyl)sulfonyl)benzenesulfonyl chloride (14) by reacting the latter with aqueous ammonium hydroxide. The reaction is typically performed in a solvent such as acetonitrile, tetrahydrofuran, ethyl acetate, isopropyl alcohol, isopropyl acetate, dimethoxyethane, dichloromethane, toluene, or mixtures thereof. (1R)-3-morpholin-4-yl-1-((phenylthio)methyl)propylamine (16), prepared as described in U.S. Pat. No. 7,390,799 B2, can be reacted with 4-fluoro-3-((trifluoromethyl)sulfonyl)benzenesulfonamide (15) in the presence of a base such as but not limited to triethylamine, to provide 4-(((1R)-3-morpholin-4-yl-1-((phenylthio)methyl)propyl)amino)-3-((trifluoromethyl)sulfonyl)benzenesulfonamide (17). The reaction is typically performed at elevated temperatures in a solvent such as but not limited to ethyl acetate.

Another route involves first reacting a reagent such as bis-(2-fluorophenyl)iodonium tetrafluoroborate (J. Org. Chem. 2008, 73, 4602) and a reagent such as sodium trifluoromethanesulfinate in the presence of a Cu(I)/Cu(III) or Pd(II)/Pd(IV) catalyst to provide 1-fluoro-2-((trifluoromethyl)sulfonyl)benzene (13). The reaction is typically performed at elevated temperatures in a solvent such as but not limited to N,N-dimethylformamide, dimethylsulfoxide, 1,4-dioxane, 1,2-dimethoxyethane, tetrahydrofuran, 1-methyl-2-pyrrolidinone, diglyme and $CH_2Cl_2$. Catalysts include but are not limited to CuI, $Cu_2O$, CuCl, copper (I) trifluoromethanesulfonate benzene complex, CuSCN Cu(OAc), $Pd(OAc)_2$ alone or in combination with ligands such as tetramethylethylenediamine, 4,4'-ditert-butyl-2,2'-dipyridyl, phenanthrolines, 2-acetylcyclohexanone, N,N-diethylsalicylamide, phosphines and the like. Other metals, such as nickel, cadmium, cobalt, tin, iron, rhodium, iridium, and platinum, or combinations thereof either in the metallic form, as salts, or complexes may also prove effective in this chemistry.

Scheme 3

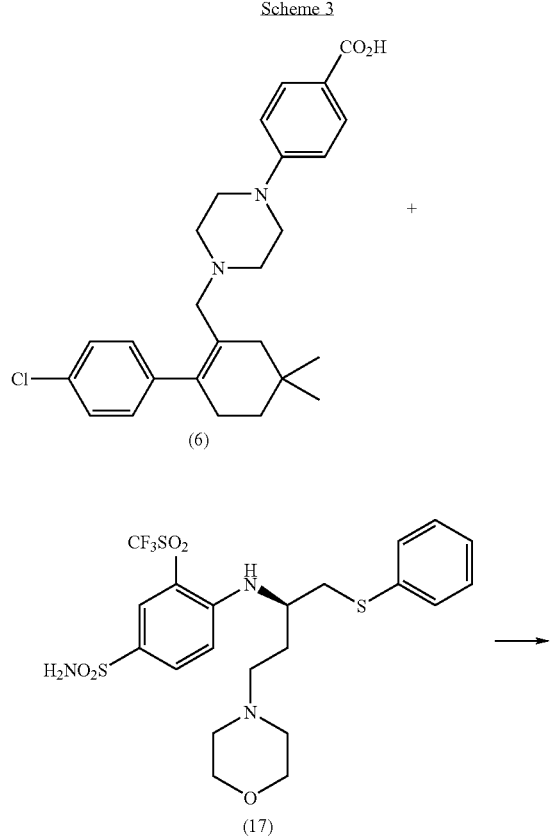

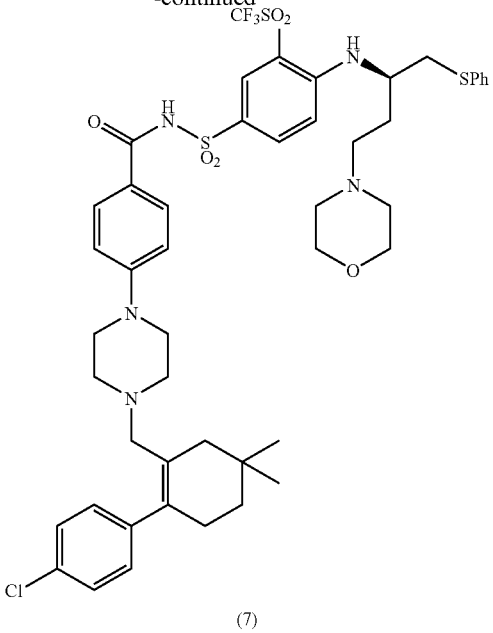

As shown in Scheme 3, 4-(4-((2-(4-chlorophenyl)-5,5-dimethylcyclohex-1-en-1-yl)methyl)piperazin-1-yl)benzoic acid (6) can be reacted with 4-(((1R)-3-morpholin-4-yl-1-((phenylthio)methyl)propyl)amino)-3-((trifluoromethyl)sulfonyl)benzenesulfonamide (17) to provide a compound such as N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (7) using methods known in the art, widely available in the literature, and as described in the example section herein.

EXPERIMENTALS

Compounds of this invention may be made by synthetic chemical processes, examples of which are shown herein. It is meant to be understood that the order of the steps in the processes may be varied, reagents, solvents, and reaction conditions may be substituted for those specifically mentioned, and vulnerable moieties may be protected and deprotected, as necessary, by NH, C(O)OH, OH, SH protecting groups.

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyl diethyl ether; DBU means 1,8-diazabicyclo(5.4.0)undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDAC.HCl means 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine.

EXAMPLE 1

(2E)-2-(hydroxymethylene)-4,4-dimethylcyclohexanone 4,4-Dimethylcyclohexanone (20 g), ethyl formate (15.8 g, 1.35 eq) and tetrahydrofuran (100 ml) were charged in a 250 ml flask and the mixture was cooled to 0-5° C. Potassium t-butoxide (1M in tetrahydrofuran 191 mL, 1.2 equiv) was slowly added while maintaining the temperature below 0° C. The reaction mixture was mixed at −5 to +5° C. and monitored for completion by GC analysis. After mixing overnight, no starting material was observed. Water (140 mL) was slowly added, and the resulting mixture was extracted with heptane (150 mL). The pH of the aqueous layer was adjusted with 6 M HCl to pH=1-2 (~40 g HCl) and the extracted with toluene (80 mL). The organic layer was washed with 20% aqueous NaCl (2×140 mL). The product solution in toluene was used directly in the next step within 12 hours (storage at 0° C.).

EXAMPLE 2

(2E)-4,4-dimethyl-2-(((triisopropylsilyl)oxy)methylene)cyclohexanone

EXAMPLE 1 (21 g as an 18% solution in toluene) was charged to a 1 L flask followed by 2-methyltetrahydrofuran (300 mL). The reaction mixture was cooled to between 0-5° C., and triethylamine (20.67 g, 1.5 equiv) was charged maintaining a reaction temperature between 0-5° C. Triisopropylsilylchloride (TIPSCl) (28.9 g, 1.1 equiv) was slowly charged, maintaining a reaction temperature between 0-5° C. The reaction mixture was mixed at a temperature range between 0-5° C. and monitored by GC for completion. Heptane (430 mL) was added, and temperature was adjusted to 10° C. Water (300 mL) was added, maintaining an internal temperature below 15° C. The reaction mixture was mixed thoroughly, and the layers were separated. The organic layer was washed with water (2×200 mL), 20% aqueous NaCl (200 mL) and 20% aqueous NaCl (360 mL). The organic layer was distilled to approximately 100 mL and chased with toluene (280 mL). The title compound was stored as a toluene solution in the refrigerator. $^1$H NMR (400 MHz, CDCl$_3$) δ 1.03 (s, 6 H) 1.07 (d, J=5.76 Hz, 14 H) 1.10 (s, 10 H) (with overlapping residual solvent resonances) 1.23 (dd, J=14.55, 6.59 Hz, 3 H) 1.26-1.29 (m, 2 H) (residual solvent) 1.64 (t, J=7.00 Hz, 2 H) 2.06 (s, 1 H), 2.26-2.28 (m, 2 H) 2.38 (t, J=7.00 Hz, 2 H) 7.55 (t, J=1.92 Hz, 1 H) ppm. Mass spec: DCI/NH$_3$ M+1=311 amu; M+NH$_3$=328 amu.

EXAMPLE 2A (2E)-4,4-dimethyl-2-(((trimethylsilyl)oxy)methylene)cyclohexanone Example 1 (0.5 g, 1 eq), 0.47 ml of triethylamine (1.05 eq) and 5 ml of anhydrous tetrahydrofuran were mixed together in a round bottom flask under N$_2$. Trimethylsilyl chloride (0.43 ml, 1.05 eq) was added drop wise at ambient temperature, and the mixture stirred at ambient temperature for 18 hours. The reaction was quenched with 10 ml of 1 N HCl and 10 ml of ethyl acetate. The organic layer was isolated and concentrated down and the residue was purified by column chromatography using 5% heptane in ethyl acetate.

EXAMPLE 3

(2E)-1-(4-chlorophenyl)-4,4-dimethyl-2-(((triisopropylsilyl)oxy)methylene)cyclohexanol To EXAMPLE 2 (26 g, as a solution in toluene) was added to anhydrous tetrahydrofuran (65 mL). The resulting mixture was cooled to −5 to 0° C. A separate flask was charged with anhydrous tetrahydrofuran (65 mL) and a 1 M solution of (4-chlorophenyl)magnesium bromide (172 mL, 2.05 equiv). The reagent mixture was cooled to −5 to 0° C. The mixture of EXAMPLE 2 in toluene was slowly added to the Grignard reagent, maintaining a reaction temperature below 5° C. The reaction was monitored by HPLC and was determined to be complete in about one hour. The reaction mixture was quenched slowly with methanol (91 mL), maintaining an internal temperature below 5° C.

EXAMPLE 4

2-(4-chlorophenyl)-5,5-dimethylcyclohex-1-ene-1-carbaldehyde

The solution from EXAMPLE 3 was slowly treated with 2N HCl (240 mL), maintaining an internal temperature below 20° C. The contents were mixed at 20° C. for 10-12 hours, and the mixture was monitored by GC analysis. Isopropyl acetate (130 mL) was charged to the reaction mixture, and the layers were mixed and separated. The organic layer was washed with water (45 mL), 1% aqueous NaHCO$_3$ (45 mL), and 20% aqueous NaCl (2×45 mL). The product mixture was azeotropically dried through a solvent exchange with toluene (125 g) to obtain a 32% solution of the title compound. $^1$H NMR (400 MHz, DMSO-d$_6$) δ 0.95 (s, 6 H) 1.48 (t, J=6.45 Hz, 2 H) 2.03 (t, J=1.92 Hz, 2 H) 2.53-2.57 (m, J=6.38, 6.38, 2.20, 2.06 Hz, 2 H) 7.36 (ddd, J=8.75, 2.54, 2.30 Hz, 2 H) 7.47 (ddd, J=8.78, 2.54, 2.26 Hz, 2 H) 9.37 (s, 1 H) ppm. Mass Spec: DCI/NH$_3$ M+1=248 amu; M+NH$_3$=266 amu.

EXAMPLE 4

2-(4-chlorophenyl)-5,5-dimethylcyclohex-1-ene-1-carbaldehyde

EXAMPLE 9 was dissolved in 50 ml tetrahydrofuran, and 40 ml 6N aqueous HCl was added. The mixture was heated to 65° C. for 17 hours. The reaction mixture was cooled, neutralized to pH~7 with 18% Na$_2$CO$_3$, extracted with ether, and washed with aqueous NaCl. The organics were concentrated to give the title compound. $^1$H NMR (400 MHz, DMSO-d$_6$) δ 0.95 (s, 6 H) 1.48 (t, J=6.45 Hz, 2 H) 2.03 (t, J=1.92 Hz, 2 H) 2.53-2.57 (m, J=6.38, 6.38, 2.20, 2.06 Hz, 2 H) 7.36 (ddd, J=8.75, 2.54, 2.30 Hz, 2 H) 7.47 (ddd, J=8.78, 2.54, 2.26 Hz, 2 H) 9.37 (s, 1 H) ppm. Mass Spec: DCI/NH$_3$ M+1=248 amu; M+NH$_3$=266 amu.

EXAMPLE 4

2-(4-chlorophenyl)-5,5-dimethylcyclohex-1-ene-1-carbaldehyde

EXAMPLE 10 (1.00 eq.), 4-chlorophenylboronic acid (1.11 eq.), tetrabutyl ammonium bromide (0.99 eq.), palladium (II) acetate (0.021 eq.), K$_2$CO$_3$ (2.45 eq.) and H$_2$O (10.0 vol.) were added together and mixed. The mixture was degassed under a cycle of high vacuum and nitrogen purge for at least three times and then warmed up to 45° C. The reaction mixture was stirred at 45° C. under nitrogen purge about 6 hours. The reaction mixture was cooled to room temperature and diluted with H$_2$O (15.0 vol.). The diluted mixture was extracted with CH$_2$Cl$_2$ (9.0 vol.×3). The CH$_2$Cl$_2$ extracts are combined and washed with H$_2$O (9.0 vol.×3) and then dried over Na$_2$SO$_4$. The solid Na$_2$SO$_4$ was filtered off and rinsed with CH$_2$Cl$_2$ (5.0 vol.). The filtrate and rinse were combined and concentrated. $^1$H NMR (400 MHz, DMSO-d$_6$) δ 0.95 (s, 6 H) 1.48 (t, J=6.45 Hz, 2 H) 2.03 (t, J=1.92 Hz, 2 H) 2.53-2.57 (m, J=6.38, 6.38, 2.20, 2.06 Hz, 2 H) 7.36 (ddd, J=8.75, 2.54, 2.30 Hz, 2 H) 7.47 (ddd, J=8.78, 2.54, 2.26 Hz, 2 H) 9.37 (s, 1 H) ppm. Mass Spec: DCI/NH$_3$ M+1=248 amu; M+NH$_3$=266 amu.

EXAMPLE 4

2-(4-chlorophenyl)-5,5-dimethylcyclohex-1-ene-1-carbaldehyde

Example 1 (2.0 g, 1 eq), 2.2 ml of triethylamine (1.2 eq) and 30 ml of anhydrous tetrahydrofuran were mixed together in a round bottom flask under N$_2$. tert-Butylchlorodimethylsilane (2.35 g, 1.2 eq) was added drop wise at ambient temperature, and the mixture was stirred at ambient temperature for 1 hour. The mixture was cooled to 0° C. and 28.6 ml of 1 M 4-chlorophenyl magnesium bromide in tetrahydrofuran was added slowly. After the addition was complete, the reaction mixture was stirred at 0° C. for 30 minutes. The reaction was quenched with 90 ml of 1 N aqueous HCl and 90 ml of ethyl acetate. The organic layer was isolated and concentrated, and the residue was purified by column chromatography using 5% heptane in ethyl acetate.

EXAMPLE 5

Ethyl 4-(4-((2-(4-chlorophenyl)-5,5-dimethylcyclohex-1-en-1-yl)methyl)piperazin-1-yl)benzoate Ethyl 4-piperazin-1-ylbenzoate (14 g) was treated with sodium triacetoxyborohydride (23 g) and then tetrahydrofuran (187 g), stirred for 15 minutes, treated with EXAMPLE 4 toluene solution (42.1 g, 32.5% aldehyde) over 20-30 minutes and stirred for 6 hours with evolution of hydrogen gas. After 12 hours, no starting material was detected by HPLC. Methyl tert-butyl ether (70 g) was added, and the reaction was quenched with 20% aqueous ammonium chloride (170 g). Again, hydrogen gas evolved. Both layers were mixed for 30 minutes and separated. The extract was washed with water (135 g), concentrated to about 115 ml, diluted with of tetrahydrofuran (125 g), concentrated to 115 ml, charged with tetrahydrofuran (125 g), concentrated to 115 ml, and charged with of ethanol (220 g), causing a solid to form. The slurry was concentrated to approximately 70 ml, charged with ethanol (165 g), and mixed for 2-3 hours (liquor concentration was 3.01 mg/mL) and filtered. The solid was washed with ethanol (2×77 g) and dried in a vacuum oven at 40° C. for 10 hours. A mixture of the solid and tetrahydrofuran (41 g) was heated at 50° C. for 30 minutes, treated with ethanol (146 g), stirred for 1 hour, cooled to 20° C. (liquor concentration was 5.12 mg/mL), and filtered. The solid was washed with ethanol (73 g) and dried in a vacuum oven at 40° C. for 10 hours. A mixture of the solid and tetrahydrofuran (37 g) was heated to 50° C. for 30 minutes, treated with of ethanol (133 g), stirred for 1 hour, cooled to 20° C. (liquor concentration was 5.1 mg/mL) and filtered. The solid was washed once with ethanol (67 g) and dried in the vacuum oven at 40° C. for 10 hours.

EXAMPLE 6

4-(4-((2-(4-chlorophenyl)-5,5-dimethylcyclohex-1-en-1-yl)methyl)piperazin-1-yl)benzoic acid 2-Methyltetrahydrofuran (20 g) and heptanes (63 g) were stirred to homogeneity for use as a product rinse. NaCl (48 g) was dissolved into water (146 g) for use in a work-up. KH$_2$PO$_4$ (40 g) and NaCl (51 g) was dissolved into water (291 g) for use in the work-up. A solution of NaOH (13 g) was dissolved in water (113 g), treated with EXAMPLE 5 and 2-methyltetrahydrofuran (125 g), stirred for 30 minutes, adjusted to 25-30° C., treated with ethanol (81 g), transferred to a flask while maintaining the internal temperature less than 35° C., adjusted to 65±5° C., stirred for at least 16 hours, until the reaction was complete by HPLC analysis (<1% EXAMPLE 5), cooled to 20° C., and settled for about 30 minutes. The lower layer was removed after sampling to assay for product loss. Part of the monobasic phosphate solution (219 g) was transferred to the reactor, and the contents were mixed for 30 minutes and settled for 30 minutes. The lower layer was removed after sampling to assay for product loss after pH determination. About half of the 25 wt % aqueous NaCl solution (91 g) was charged to the reactor, and the contents were stirred for at least 15 minutes and settled for 15 minutes. The lower layer was transferred to drums after sampling for product losses, and the remaining 25 wt % NaCl solution (about 97 g) was charged to the reactor. The contents were mixed for at least 15 minutes and allowed to settle for at least 1 hour. The lower layer was transferred to drums after sampling for product losses. 2-Methyltetrahydrofuran (125 g) was charged to the reactor, and the contents were stirred for at least 10 minutes. The product solution was transferred through a nylon filter into the rinsed reactor using 2-methyltetrahydrofuran to rinse the canisters (4 g 2-methyltetrahydrofuran per canister) and distilled under vacuum at a jacket temperature of about 40° C. to about 214 ml. While maintaining vacuum and a volume of about 214 ml, 2-methyltetrahydrofuran (375 g) was added in portions to azeotropically dry the product solution. This solution was sampled during the distillation to determine moisture content (target<1% water). The solution was concentrated under vacuum to approximately 73 ml, and the internal temperature was adjusted to about 45° C. (target: 40° C.). The contents were stirred for 1 hour, treated with heptanes (172 g) over 30 minutes, and stirred at about 45° C. (target:40° C.) for 2 hours and about 25° C. (target: 20° C.) for 2 hours. The product suspension was distilled under vacuum to 140 ml, and the internal temperature was adjusted to about 25° C. (target: 20° C.). The mixture was vacuum filtered, and the liquors were recycled one time to rinse the flask. The filtrate was rinsed with a portion of the heptane/2-methyltetrahydrofuran solution (41 g), allowing the rinse to sit on the cake for at least 15 minutes before applying vacuum. The rinse was repeated with the remaining heptane/2-methyltetrahydrofuran solution (about 22 g), again allowing the rinse to sit on the cake for at least 15 minutes before applying vacuum. The liquors and rinses were sampled separately for product loss assays. The filter pot was purged for at least 2 hours with nitrogen, and the product was transferred to a dryer and dried under vacuum with a nitrogen bleed at less than or equal to 40° C. (target: 35° C.), for at least 12 hours.

EXAMPLE 7

N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl) benzenesulfonamide A mixture of 4-(((1R)-3-morpholin-4-yl-1-((phenylthio) methyl)propyl)amino)-3-((trifluoromethyl)sulfonyl)benzenesulfonamide (8.575 g) (EXAMPLE 17), EXAMPLE 6 (6.4 g), 4-dimethylaminopyridine (4.4 g), 1-ethyl-3-(3-(dimethylamino)propyl)carbodiimide hydrochloride (4.1 g) and dichloromethane (80 g) was heated at 30° C., cooled to room temperature, quenched with N,N-dimethylethylenediamine (1.1 g), distilled to 30 ml, treated with water (5.4 g) and ethyl acetate (97 g), distilled to 65 ml, treated with water (5.4 g) and ethyl acetate (97 g), distilled to 80 ml and treated with 10% acetic acid/0.75% brine (182 g) and ethyl acetate (65 g). The layers were separated, and the extract was washed with 10% aqueous acetic acid/0.75% brine (182 g), 25% aqueous $K_2HPO_4$ (180 g) and pH 7 buffer solution (163 g), concentrated to 35 ml and chase distilled with ethyl acetate (120 g, 120 g and 60 g) with concentration to 35 ml after each addition. The extract was then treated with ethyl acetate (60 g), and the solution was diluted with ethanol (71 g) and polish-filtered through a polypropylene 0.5 μm filter into a reactor with an ethyl acetate (20 g) rinse. In a separate reactor, HCl (2.8 g) in ethanol (80 g) was prepared and polish-filtered through a separate filter and housing into the reactor. The polish filtration of the solution removed residual phosphate salts from the final extraction. The solution was concentrated to about 150 ml and maintained at that level while an additional chase of ethanol (160 g) was conducted, heated at 45° C., treated with seeds (90 mg) in ethanol (1 g), stirred for 12 hours, cooled to 20° C. and stirred for another 4 hours. Analysis of the filtrates indicated the crystallization was complete. The slurry was filtered, and the solids were rinsed with ethanol (2×57 g). The rinses were applied in a slurry fashion with no vacuum, (contact time 15-25 minutes for each) then removed by vacuum filtration. The wet cake was sampled for impurities to determine if a recrystallization would be necessary. The solids were dried under vacuum and nitrogen at 50° C. for 3 days. Analysis of the dryer sample (GPAS residual solvents method) showed that drying was complete. $^1$H NMR (400 MHz, methanol-$d_4$) δ ppm 1.08 (s, 5 H) 1.57 (t, J=6.38 Hz, 2 H) 2.11 (s, 2 H) 2.26-2.34 (m, 1 H) 2.40 (t, J=5.69 Hz, 2 H) 3.18-3.27 (m, 4 H) 3.42 (dd, J=14.48, 4.87 Hz, 2 H) 3.69 (s, 2 H) 3.87 (s, 2 H) 4.14 (s, 1 H) 6.99 (td, J=6.07, 2.54 Hz, 3 H) 7.11-7.19 (m, 5 H) 7.29-7.32 (m, 2 H) 7.37-7.41 (m, 2 H) 7.76 (d, J=9.06 Hz, 2 H) 8.07 (dd, J=9.19, 2.33 Hz, 1 H) 8.29 (d, J=2.20 Hz, 1 H).

EXAMPLE 8

2-(diethoxymethyl)-4,4-dimethylcyclohexanone

To 34 ml of $HC(OCH_2CH_3)_3$ (0.2 mol) at −38° C. was added drop wise a solution of 31 ml $BF_3(OCH_2CH_3)_2$ in 90 ml $CH_2Cl_2$ (0.24 mol) over 15 minutes at about −30°C. The mixture was warmed to 0° C. and mixed for 10 minutes to form diethoxycarbenium fluoroborate. The mixture was cooled to −78° C., and 12.6 g dimethylcyclohexanone in 40 ml $CH_2Cl_2$ (0.1 mol) was added, followed by drop wise addition of 52 ml N,N-diisopropylethylamine(0.3 mol) over 30 minutes. The mixture stirred at −78° C. for 1.5 hours. The cold reaction was quenched into 1000 g aqueous 6.5% $NaHCO_3$. Dichloromethane (250 ml) was added and the mixture was stirred vigorously for 10 minutes. The organics were washed with 400 g cold aqueous 1% $H_2SO_4$ and then with 400 g cold water. The organics were dried over $MgSO_4$, filtered, and the filtrate was concentrated to give the title compound. GCMS: 183 (ms/z).

EXAMPLE 9

1-(4-chlorophenyl)-2-(diethoxymethyl)-4,4-dimethylcyclohexanol

EXAMPLE 8 was dissolved in 200 ml tetrahydrofuran, cooled to −78° C., and 195 ml 1M chlorophenyl magnesium bromide (0.2 mol) was added over 25 minutes. The mixture was mixed at about −20° C. for 2 hours. The reaction mixture was quenched with 200 g 20% aqueous $NH_4Cl$ at about −7° C., extracted with 400 ml ethyl acetate, then washed with 20% aqueous $NH_4Cl$, 5% aqueous $NaHCO_3$, and 25% aqueous NaCl. The organics were concentrated to provide the title compound.

EXAMPLE 10

2-chloro-5,5-dimethylcyclohex-1-enecarbaldehyde

A solution of N,N-dimethylformamide (1.37 eq.) in $CH_2Cl_2$ (1.5 vol.) was cooled to 0° C. and then $POCl_3$ (1.25 eq.) was added slowly to the N,N-dimethylformamide solution at below 25° C. The resulting solution was allowed to warm up to room temperature. A solution of 4,4-dimethylcyclohexanone (1.00 eq.) in $CH_2Cl_2$ (1.4 vol.) was added slowly to the above solution at below 30° C., and then the reaction mixture was stirred at 45° C. overnight. The reaction mixture was quenched into a cooled 10% sodium acetate solution (30.0 vol.) at below 15° C., followed by a $CH_2Cl_2$ rinse (4.6 vol.). The quenched mixture was stirred while allowing it to warm up to room temperature. The organic layer was separated and then aqueous layer was extracted with $CH_2Cl_2$ (7.6 vol.×3). The organic layer and $CH_2Cl_2$ extracts were combined and concentrated to give a solution and the solution was used in the next step without purification. $^1$H NMR (400 MHz, $CDCl_3$) δ 10.1 (1H, s, CHO) $^1$H NMR (400 MHz, $CDCl_3$) δ 10.1 (1H, s, CHO), 2.61-2.57 (2H, m), 2.09 (2H, s), 1.54-1.51 (2H, m), 0.95 (6H, s).

EXAMPLE 11

2-fluorobenzenesulfonyl chloride

The title compound was purchased commercially from Sigma-Aldrich.

EXAMPLE 12

2-fluorobenzenesulfonyl fluoride

A 100-L round bottomed flask fitted with overhead stirrer, nitrogen inlet, temperature probe and ice bath was charged with 2-fluorobenzenesulfonyl chloride (50 g) and tetrahydrofuran (220 g). The solution was cooled down to −5° C. with an ice bath. Tetrabutylammonium fluoride (270 mL of 1M in tetrahydrofuran solution) was added slowly to the reactor. The internal temperature was kept less than 8° C. After the addition was completed, HPLC showed the reaction was completed. The reaction was quenched by slowly adding 250 g of water. Then 430 g of toluene was added to the reaction mixture. The layers were separated. The organic layer was washed with 250 g of water twice. The organic layer was distilled down under vacuum with the bath temperature at 48° C. $^1$H NMR (400 MHz, CDCl$_3$) δ 8.01-7.96 (m, 1H), 7.76-7.83 (m, 1H), 7.32-7.44 (m, 2H).

EXAMPLE 13

1-fluoro-2-((trifluoromethyl)sulfonyl)benzene

The solution of EXAMPLE 12 (44.3 g) in a solution of 450 ml was added to a round bottomed flask fitted with overhead stirrer, nitrogen inlet, cold-water bath and temperature probe. It was cooled down to 12° C. (((CH$_3$)$_2$N)$_3$S)$^+$(F$_2$Si(CH$_3$)$_3$)$^-$, also known as TASF (6.1 g), was added in one portion. Ruppert's reagent (370 g, CH$_3$SiCF$_3$) was charged slowly to the reaction mixture while maintaining the internal temperature less than 23° C. The reaction was completed after addition. Water (220 g) was added to quench the reaction, the layers were separated, and the organic layer was washed twice with 220 g of water. The organic solution was distilled under vacuum with the bath temperature at 50° C. Heptanes (500 g) were added to the residue, and the mixture was distilled down until the solvent was removed. $^1$H NMR (400 MHz, CDCl$_3$) δ 8.01-8.05 (m, 1H), 7.84-7.87 (m, 1H), 7.44-7.48 (m, 1H), 7.36-7.39 (m 1H).

EXAMPLE 13

1-fluoro-2-((trifluoromethyl)sulfonyl)benzene

A 1 L three-neck round bottom flask equipped with a magnetic stir bar and a J-Chemthermocouple was charged with sodium trifluoromethanesulfinate (9.29 g, 59.5 mmol), bis-(2-fluorophenyl)iodonium tetrafluoroborate (18.5 g, 45.8 mmol) (J. Org. Chem. 2008, 73, 4602) and copper(I) oxide (0.131 g, 0.92 mmol). The flask was purged with nitrogen for 30 minutes. Degassed N,N-dimethylformamide (225 mL) was added to the flask and the reaction mixture was stirred at 50° C. for 16 hours under a positive atmosphere of nitrogen. The reaction mixture was cooled to the room temperature, diluted with 500 mL isopropyl acetate and transferred to a 2 L separatory funnel. The organic layer was washed with 500 mL of 5% aqueous K$_2$CO$_3$ solution. The organic layer was washed with water (500 mL×2) followed by a wash with 250 mL brine. The organic layer was dried over magnesium sulfate, filtered through diatomaceous earth and concentrated in vacuo to obtain the title compound. The product was further purified by distillation. $^1$H NMR (500 MHz, CDCl$_3$) δ 8.03 (t, J=7.3, 1H), 7.85 (dd, J=7.5, 13.2, 1H), 7.45 (t, J=7.7, 1H), 7.36 (t, J=9.1, 1H). $^{19}$F NMR (470 MHz, CDCl$_3$) δ 77.4 (d, J=9.4, 3F), d 102.7 (m, 1F). HPLC: Zorbax SB-C18 4.6×150 mm, 3.5 µm, method: 90% of 0.1% H$_3$PO$_4$ and 10% CH$_3$CN, ramped to 90% CH$_3$CN over 7 minutes, held for 3 minutes, ramped to 10% CH$_3$CN over 1 minutes; peak at 6.58 minutes.

EXAMPLE 13

1-fluoro-2-((trifluoromethyl)sulfonyl)benzene

Mesityl-2-fluorophenyl iodonium triflate (Sanford M et al. JACS, 2005, 127, 7330 and Widdowson, D. et al. Tetrahedron Letters 2000, 41, 5393.) (0.1 g, 0.204 mmol), sodium trifluoromethanesulfinate (0.035 g, 0.224 mmol) and copper(I) oxide (2.92 mg, 0.020 mmol) were weighed into a reactor equipped with a magnetic stir bar. N,N-dimethylformamide (1 mL) was added, the reactor was capped and heated at 25° C. for 24 hours. HPLC analysis of the crude reaction mixture indicated the formation of the title compound.

EXAMPLE 14

4-fluoro-3-((trifluoromethyl)sulfonyl)benzenesulfonyl chloride

EXAMPLE 13 (80 g) was charged to a reactor fitted with overhead stirrer, nitrogen inlet, condenser, scrubber, temperature probe and heating bath. Chlorosulfonic acid (307 g) was added slowly through an additional funnel. The mixture was then heated up to 120° C. and held for 22 hours at 120° C. The mixture was cooled down to room temperature. Thionyl chloride (118 g) was added to the reaction mixture in one portion at ambient temperature. The mixture was stirred at 25° C. for 24 hours. A sample was pulled and HPLC showed the reaction was completed with 1.1% of the sulfonic acid left. Isopropyl acetate (775 g) was cooled down to −50° C. Water (600 g) was charged to isopropyl acetate solution. The reaction mixture was transferred slowly to the isopropyl acetate/ice mixture through an additional funnel. The internal temperature increased to 0.8° C. during the addition. The cold reaction mixture was warmed up 15° C. and layers were separated. The organic layer was used in the next step (EXAMPLE 15) without isolation.

EXAMPLE 15

4-fluoro-3-((trifluoromethyl)sulfonyl)benzenesulfonamide

The solution from EXAMPLE 14 was charged into a flask fitted with overhead stirrer, nitrogen inlet, temperature probe and cooling bath. The solution was cooled down to −50° C. using an acetone/dry ice bath. Ammonium hydroxide (238 g) solution was slowly added to the reaction mixture through an additional funnel. The internal temperature was kept at about −40° C. HPLC showed the reaction was completed. The solution was cooled down to −60° C. 6 N HCl (600 g) was added to the reaction mixture slowly to keep the temperature under −35° C. The mixture was warmed up to room temperature. The layers were separated, and the organic layer was washed twice with 375 g of 4 N HCl. The organic layer was distilled down under vacuum with bath temperature from 40 to 50° C. Toluene (700 g) was added to the residue, and the mixture was stirred at room temperature for an hour. The mixture was filtered and washed with toluene to obtain the title compound.

EXAMPLE 16

(1R)-3-morpholin-4-yl-1-((phenylthio)methyl)propylamine

The title compound can be prepared as described in U.S. Pat. No. 7,390,799 B2.

EXAMPLE 17

4-(((1R)-3-morpholin-4-yl-1-((phenylthio)methyl)propyl)amino)-3-((trifluoromethyl)sulfonyl)benzenesulfonamide The title compound can be prepared as described in U.S. Pat. No. 7,390,799 B2.

The preceding is meant to be illustrative of this invention and not limiting. Obvious variations and changes are meant to be within the scope of this invention, as defined in the claims.

We claim:

1. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:
   (e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;
   (f) reacting ethyl 4-(4-((2-(4-chlorophenyl)-5,5-dimethylcyclohex-1-en-1-yl)methyl)piperazin-1-yl)benzoate and an aqueous base, and isolating or not isolating the 4-(4-((2-(4-chlorophenyl)-5,5-dimethylcyclohex-1-en-1-yl)methyl)piperazin-1-yl)benzoic acid; and
   (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide and a first coupling reagent with or without a base and with or without an auxiliary coupling reagent, and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

2. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, or a pharmaceutically acceptable salt thereof, comprising:
   (e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;
   (f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and
   (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

3. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:
   (a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;
   (b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;
   (c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and
   (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;
   (e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;
   (f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid; and
   (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

4. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:
   (a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;
   (b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

5. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and a first fluoride source to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and a second fluoride source to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-(trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

6. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid;

(m) reacting 2-fluorobenzenesulfonyl chloride, and tetra-n-butylammonium fluoride to provide 2-fluorobenzenesulfonyl fluoride and isolating or not isolating the 2-fluorobenzenesulfonyl fluoride;

(n) reacting the 2-fluorobenzenesulfonyl fluoride, Ruppert's reagent ($CH_3SiCF_3$), and tris(dimethylamino)sulfonium difluorotrimethylsilicate to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

7. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, an alkyl formate and a first base to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, a second base and a first silyl ether protecting group reagent to provide a first protected (2E)-2-(hydroxymethylene)-4,4-dimethylcyclohexanone and isolating or not isolating the first protected (2E)-2-(hydroxymethylene)-4,4-dimethylcyclohexanone;

(c) reacting the first protected (2E)-2-(hydroxymethylene)-4,4-dimethylcyclohexanone and 4-chlorophenyl magnesium bromide to provide the first protected (2E)-1-(4-chlorophenyl)-2-(hydroxymethylene)-4,4-dimethylcyclohexanol; and isolating or not isolating the first protected (2E)-1-(4-chlorophenyl)-2-(hydroxymethylene)-4,4-dimethylcyclohexanol; and (d) reacting the first protected (2E)-1-(4-chlorophenyl)-2-(hydroxymethylene)-4,4-dimethylcyclohexanol and a first acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and a first reducing agent and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and an aqueous third base, and isolating or not isolating the 4-(4-((2-(4-chlorophenyl)-5,5-dimethylcyclohex-1-en-1-yl)methyl)piperazin-1-yl)benzoic acid;

(r) reacting a first metal trifluoromethanesulfinate, a first aryl fluoride source, and a first catalyst to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and a first $NH_3$ source to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and a sixth base to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, a first coupling reagent, and, optionally; a first auxiliary coupling reagent and isolating or not isolating the N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide.

8. A process for making N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, comprising:

(a) reacting 4,4-dimethylcyclohexanone, ethyl formate and potassium tert-butoxide to provide (2E)-2-(hydroxymethylene)-4,4-dimethylcyclohexanone and isolating or not isolating the (2E)-2-(hydroxymethylene)-4,4-dimethylcyclohexanone;

(b) reacting the (2E)-2-(hydroxymethylene)-4,4-dimethylcyclohexanone, triethylamine and trimethylchlorosilane, tert-butylchlorodimethylsilane, or triisopropylchlorosilane to provide (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and isolating or not isolating the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone;

(c) reacting the (2E)-4,4-dimethyl-2-(((triisopropylsilyl)oxy)methylene)cyclohexanone, (2E)-4,4-dimethyl-2-(((trimethylsilyl)oxy)methylene)cyclohexanone, or (2E)-2-(((tert-butyl(dimethyl)silyl)oxy)methylene)-4,4-dimethylcyclohexanone and 4-chlorophenyl magnesium bromide to provide ((2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol; and isolating or not isolating the (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol;

(d) reacting (2E)-1-(4-chlorophenyl)-4,4-dimethyl-2-(((triisopropylsilyl)oxy)methylene)cyclohexanol, (2E)-1-(4-chlorophenyl)-4,4-dimethyl-2-(((trimethylsilyl)oxy)methylene)cyclohexanol, or (2E)-2-(((tert-butyl(dimethyl)silyl)oxy)methylene)-1-(4-chlorophenyl)-4,4-dimethylcyclohexanol and hydrochloric acid to provide 2-(4-chlorophenyl)-5,5-dimethylcyclohex-1-ene-1-carbaldehyde and isolating or not isolating the 2-(4-chlorophenyl)-5,5-dimethylcyclohex-1-ene-1-carbaldehyde;

(e) reacting 2-(4-chlorophenyl)-5,5-dimethylcyclohex-1-ene-1-carbaldehyde, ethyl 4-piperazin-1-ylbenzoate and sodium triacetoxyborohydride and isolating or not isolating the ethyl 4-(4-((2-(4-chlorophenyl)-5,5-dimethylcyclohex-1-en-1-yl)methyl)piperazin-1-yl)benzoate;

(f) reacting ethyl 4-(4-((2-(4-chlorophenyl)-5,5-dimethylcyclohex-1-en-1-yl)methyl)piperazin-1-yl)benzoate and aqueous sodium hydroxide, and isolating or not isolating the 4-(4-((2-(4-chlorophenyl)-5,5-dimethylcyclohex-1-en-1-yl)methyl)piperazin-1-yl)benzoic acid;

(r) reacting sodium trifluoromethanesulfinate, bis-(2-fluorophenyl)iodonium tetrafluoroborate and copper(I) oxide to provide 1-fluoro-2-((trifluoromethyl)sulfonyl)benzene and isolating or not isolating the 1-fluoro-2-((trifluoromethyl)sulfonyl)benzene;

(o) reacting 1-fluoro-2-((trifluoromethyl)sulfonyl)benzene, and chlorosulfonic acid to provide 4-fluoro-3-((trifluoromethyl)sulfonyl)benzenesulfonyl chloride and isolating or not isolating the 4-fluoro-3-((trifluoromethyl)sulfonyl)benzenesulfonyl chloride;

(p) reacting 4-fluoro-3-((trifluoromethyl)sulfonyl)benzenesulfonyl chloride, and aqueous ammonium hydroxide to provide 4-fluoro-3-((trifluoromethyl)sulfonyl)benzenesulfonamide and isolating or not isolating the 4-fluoro-3-((trifluoromethyl)sulfonyl)benzenesulfonamide;

(q) reacting 4-fluoro-3-((trifluoromethyl)sulfonyl)benzenesulfonamide, (1R)-3-morpholin-4-yl-1-((phenylthio)methyl)propylamine and triethylamine to provide 4-(((1R)-3-morpholin-4-yl-1-((phenylthio)methyl)propyl)amino)-3-((trifluoromethyl)sulfonyl)benzenesulfonamide and isolating or not isolating the 4-(((1R)-3-morpholin-4-yl-1-((phenylthio)methyl)propyl)amino)-3-((trifluoromethyl)sulfonyl)benzenesulfonamide; and (g) reacting 4-(4-((2-(4-chlorophenyl)-5,5-dimethylcyclohex-1-en-1-yl)methyl)piperazin-1-yl)benzoic acid, 4-(((1R)-3-morpholin-4-yl-1-((phenylthio)methyl)propyl)amino)-3-((trifluoromethyl)sulfonyl)benzenesulfonamide, 1-ethyl-3-(3-(dimethylamino)propyl)-carbodiimide hydrochloride, and 4-dimethylaminopyridine and isolating or not isolating the N-(4-(4-((2-(4-chlorophenyl)-5,5-dimethyl-1-cyclohex-1-en-1-yl)methyl)piperazin-1-yl)benzoyl)-4-((((1R)-3-(morpholin-4-yl)-1-((phenylsulfanyl)methyl)propyl)amino)-3-((trifluoromethyl)sulfonyl)benzenesulfonamide.

9. A compound, or a pharmaceutically acceptable salt thereof, selected from the group consisting of (2E)-4,4-dimethyl-2-(((triisopropylsilyl)oxy)methylene)cyclohexanone, (2E)-4,4-dimethyl-2-(((trimethylsilyl)oxy)methylene)cyclohexanone, and (2E)-2-(((tert-butyl(dimethyl)silyl)oxy)methylene)-4,4-dimethylcyclohexanone.

10. The compound 2-(4-chlorophenyl)-5,5-dimethylcyclohex-1-ene-1-carbaldehyde or a pharmaceutically acceptable salt thereof.

* * * * *

UNITED STATES PATENT AND TRADEMARK OFFICE
CERTIFICATE OF CORRECTION

PATENT NO. : 8,168,784 B2  
APPLICATION NO. : 12/486361  
DATED : May 1, 2012  
INVENTOR(S) : Franczyk, II et al.

Page 1 of 1

It is certified that error appears in the above-identified patent and that said Letters Patent is hereby corrected as shown below:

In the Specifications

Column 1, line 7, related U.S. application data, "61/074390," to read as --61/074,390--

In the Claims

Column 66, line 38, claim 3: "optionally;" to read as --optionally,--

Column 67, line 6, claim 4: "((2E)-1-(4-chlorophenyl)" to read as --(2E)-1-(4-chlorophenyl)--

Column 68, line 40, claim 5: "3- ((trifluoromethyl)" to read as --3-((trifluoromethyl)--

Column 68, line 56, claim 5: "optionally;" to read as --optionally,--

Column 69, line 25, claim 6: "((2E)-1-(4-chlorophenyl)" to read as --(2E)-1-(4-chlorophenyl)--

Column 71, line 34, claim 7: "optionally;" to read as --optionally,--

Column 72, line 2, claim 8: "((2E)-1-(4-chlorophenyl)" to read as --(2E)-1-(4-chlorophenyl)--

Signed and Sealed this  
Sixth Day of May, 2014

Michelle K. Lee  
*Deputy Director of the United States Patent and Trademark Office*